(12) United States Patent
Yu et al.

(10) Patent No.: US 12,178,625 B2
(45) Date of Patent: Dec. 31, 2024

(54) RADIATION SYSTEMS, METHODS, AND DEVICES

(71) Applicant: SHANGHAI UNITED IMAGING HEALTHCARE CO., LTD., Shanghai (CN)

(72) Inventors: Qiang Yu, Shanghai (CN); He Zhu, Shanghai (CN); Zhanqiang Kong, Shanghai (CN); Wenqiang Liu, Shanghai (CN); Zhenwei Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 314 days.

(21) Appl. No.: 17/660,415

(22) Filed: Apr. 24, 2022

(65) Prior Publication Data
US 2022/0249042 A1   Aug. 11, 2022

Related U.S. Application Data

(63) Continuation of application No. PCT/CN2020/123781, filed on Oct. 26, 2020.

(30) Foreign Application Priority Data

Oct. 24, 2019   (CN) .......................... 201911017307.1
Nov. 26, 2019   (CN) .......................... 201911176115.5
Dec. 23, 2019   (CN) .......................... 201911342081.2

(51) Int. Cl.
*A61B 6/00*   (2024.01)
*B60B 33/00*   (2006.01)
(Continued)

(52) U.S. Cl.
CPC ............ *A61B 6/4405* (2013.01); *A61B 6/447* (2013.01); *B60B 33/0078* (2013.01);
(Continued)

(58) Field of Classification Search
CPC ....... A61B 6/4405; A61B 6/447; A61B 6/105; A61B 6/4411; A61N 2005/0633
See application file for complete search history.

(56) References Cited

U.S. PATENT DOCUMENTS 5,081,662 A    1/1992  Warden et al.
2014/0098942 A1   4/2014  Omura et al.
(Continued)

FOREIGN PATENT DOCUMENTS

CN    101347336 A    1/2009
CN    201267480 Y    7/2009
(Continued)

OTHER PUBLICATIONS

The Extended European Search Report in European Application No. 20880245.4 mailed on Jan. 3, 2024, 15 pages.
(Continued)

*Primary Examiner* — David P Porta
*Assistant Examiner* — Casey Bryant
(74) *Attorney, Agent, or Firm* — METIS IP LLC

(57) ABSTRACT

The present disclosure provides a gantry for an X-ray system. The gantry may include a base section, a lifting section, and a swing section. The base section may be configured to move. A first end of the lifting section may be connected to the base section. A first end of the swing section may be rotatably connected to a second end of the lifting section. A radiation assembly may be disposed on a second end of the swing section.

20 Claims, 15 Drawing Sheets

(51) Int. Cl.
  *F16M 11/10* (2006.01)
  *F16M 11/42* (2006.01)
(52) U.S. Cl.
  CPC ............ *F16M 11/10* (2013.01); *F16M 11/42* (2013.01); *F16M 2200/021* (2013.01); *F16M 2200/066* (2013.01)

(56) References Cited

U.S. PATENT DOCUMENTS

| | | |
|---|---|---|
| 2015/0069256 A1 | 3/2015 | Nakata et al. |
| 2015/0270022 A1 | 9/2015 | Omura |
| 2016/0045174 A1 | 2/2016 | Wendlandt et al. |
| 2016/0345928 A1 | 12/2016 | Jung et al. |
| 2017/0000449 A1 | 1/2017 | Tsujii et al. |
| 2018/0125439 A1* | 5/2018 | Nabeta ................. A61B 6/4405 |
| 2018/0235558 A1 | 8/2018 | Onobori et al. |
| 2019/0021686 A1* | 1/2019 | Ogura .................. A61B 6/4405 |
| 2020/0155091 A1* | 5/2020 | Dirisio .................... F16D 59/02 |

FOREIGN PATENT DOCUMENTS

| | | | |
|---|---|---|---|
| CN | 202235431 U | 5/2012 | |
| CN | 202446409 U | 9/2012 | |
| CN | 203591267 U | 5/2014 | |
| CN | 203739775 U | 7/2014 | |
| CN | 103963694 A | 8/2014 | |
| CN | 104228822 A | 12/2014 | |
| CN | 104398265 A | 3/2015 | |
| CN | 204246145 U | 4/2015 | |
| CN | 204318772 U | 5/2015 | |
| CN | 105982679 A | 10/2016 | |
| CN | 106264574 A | 1/2017 | |
| CN | 206404185 U | 8/2017 | |
| CN | 208426131 U | 1/2019 | |
| CN | 209032408 U | 6/2019 | |
| CN | 110179491 A | 8/2019 | |
| CN | 110742641 A | 2/2020 | |
| CN | 110840474 A | 2/2020 | |
| CN | 111022905 A | 4/2020 | |
| CN | 211674281 U | * 10/2020 | |
| CN | 116570306 A | * 8/2023 | ............. A61B 6/022 |
| EP | 3323345 A1 | 5/2018 | |
| JP | 2007210579 A | 8/2007 | |
| JP | 5797058 B2 | 10/2015 | |
| KR | 20140112802 A | 9/2014 | |
| WO | 9014748 A1 | 11/1990 | |
| WO | 2010128556 A1 | 11/2010 | |

OTHER PUBLICATIONS

The Fourth Office Action in Chinese Application No. 201911176115.5 mailed on Aug. 3, 2022, 19 pages.
Partial Supplementary European Search Report in European Application No. 20880245.4 mailed on Oct. 24, 2022, 12 pages.
International Search Report in PCT/CN2020/123781 mailed on Jan. 27, 2021, 5 pages.
Written Opinion in PCT/CN2020/123781 mailed on Jan. 27, 2021, 5 pages.
First Office Action in Chinese Application No. 201911176115.5 mailed on Mar. 25, 2021, 16 pages.
The Second Office Action In Chinese Application No. 201911176115.5 mailed on Aug. 20, 2021, 19 pages.

* cited by examiner

RADIATION SYSTEMS, METHODS, AND DEVICES

CROSS-REFERENCE TO RELATED APPLICATIONS

This application is a continuation of International Patent Application No. PCT/CN2020/123781, filed on Oct. 26, 2020, which claims priority to Chinese Patent Application No. 201911017307.1 filed on Oct. 24, 2019, Chinese Patent Application No. 201911176115.5 filed on Nov. 26, 2019, and Chinese Patent Application No. 201911342081.2 filed on Dec. 23, 2019, the contents of each of which are hereby incorporated by reference to its entirety.

TECHNICAL FIELD

The present application generally relates to medical devices, and more particularly, to radiation systems, methods, and devices.

BACKGROUND

A radiation device (e.g., a medical imaging device, a radiotherapy device) is widely used in medical diagnosis and therapy. In a stressed environment such as a field rescue camp, due to an uneven ground and a limited space, a large-scale radiation device may be too bulky to be moved and/or positioned fast, which may affect a rescue work of medical staff.

SUMMARY

According to one aspect of the present disclosure, a gantry for an X-ray system is provided. The gantry may include a base section, a lifting section, and a swing section. The base section is configured to move. A first end of the lifting section may be connected to the base section. A first end of the swing section may be rotatably connected to a second end of the lifting section. A radiation assembly may be disposed on a second end of the swing section.

In some embodiments, the base section may include a base frame and a transfer wheel assembly. The lifting section may be connected to the base frame, and the transfer wheel assembly may be connected to the base frame.

In some embodiments, the transfer wheel assembly may include at least one of a fixing wheel, a movable wheel, or a lock assembly. The fixing wheel may be fixedly connected to the base frame. The movable wheel may be rotatably connected to the base frame, and receives the fixing wheel therein. The lock assembly may be connected to the fixing wheel and configured to control a movement of the movable wheel such that the movable wheel is static relative to the fixing wheel when the lock assembly is in a locked configuration. The lock assembly may also be configured to control the movement of the movable wheel such that the movable wheel moves relative to the fixing wheel when the lock assembly is in an unlocked configuration.

In some embodiments, the lock assembly may include at least one of a master rod, a slave rod, a transmission rod, or a driving unit. The master rod may be disposed on the fixing wheel via a rotation shaft. The slave rod may include a fixing end and a rotation end, the fixing end being rotatably connected to the fixing wheel. A first end of the transmission rod may be rotatably connected to the master rod. A second end of the transmission rod may be connected to the rotation end of the slave rod. The driving unit may be connected to the rotation shaft and configured to drive a rotation of the master rod and cause the slave rod to press against the movable wheel when the rotation of the master rod causes the lock assembly to be in the locked configuration. The driving unit may also be configured to drive the rotation of the master rod and disengage the slave rod from the movable wheel when the rotation of the master rod causes the lock assembly to be in the unlocked configuration.

In some embodiments, the transfer wheel assembly may include a first transfer wheel and a second transfer wheel. The first transfer wheel may be disposed on a first side of the base frame. The second transfer wheel may be disposed on a second side of the base frame. The first side of the base frame may be opposite to the second side of the base frame. A first lock assembly disposed on the first transfer wheel and a second lock assembly disposed on the second transfer wheel may share one driving unit.

In some embodiments, the base section further may include a support assembly. The support assembly may include a support rod, a support wheel, and a locking unit. An end of the support rod may be rotatably connected to the base frame. The support wheel may be disposed on the support rod and configured to support the support rod. The locking unit may be disposed between the support rod and the base frame and configured to lock the support rod on the base frame.

In some embodiments, the locking unit may include a first lock block, a second lock block, and a lock nut. The first lock block may be connected to the support rod and may include a first protrusion or a first groove. The second lock block may be connected to the base frame and may include a second protrusion or a second groove. The lock nut may include a threaded connection that is configured to connect the first lock block and the second lock block.

In some embodiments, the lifting section may include a fixed sleeve, a support sliding rod, a lifting unit, and a first pneumatic support rod. A first end of the fixed sleeve may be connected to the base section, and a second end of the fixed sleeve may be open. The support sliding rod may be disposed within a chamber of the fixed sleeve. The lifting unit may be connected to an end of the support sliding rod. The end of the support sliding rod may extend beyond the fixed sleeve. The lifting unit may be connected to the swing section. The first pneumatic support rod may be disposed within the chamber of the fixed sleeve. A first end of the first pneumatic support rod may be connected to the base section. A second end of the first pneumatic support rod may be connected to the support sliding rod.

In some embodiments, the swing section may include a swing arm and a second pneumatic support rod. A first end of the swing arm may be connected to the second end of the lifting section. The radiation assembly may be disposed on a second end of the swing arm. The second pneumatic support rod may be disposed between the swing arm and the lifting section. A pulling force may be exerted on the second pneumatic support rod when the swing arm swings upward.

In some embodiments, the gantry may further include a safety protection section, and the safety protection section may be configured to lock at least one of the lifting section and the swing section.

In some embodiments, the safety protection section may include a loading unit and a lock assembly. The loading unit may be configured to load an external component, the external component including the radiation assembly. The lock assembly may include a first lock, a second lock, a first sub-locking unit, and a second sub-locking unit. The second lock may be disposed on the loading unit. The first sub-locking unit may be configured to lock the first lock and the second lock. The second sub-locking unit may be configured to lock the first sub-locking unit. The external component may drive the second sub-locking unit to unlock the first sub-locking unit when the external component is loaded on the loading unit.

In some embodiments, the second sub-locking unit may include a locking part, a locking rod, and an elastic part. The locking rod may be connected to the locking part. The elastic part may be configured to drive the locking part to be reset. The external component may drive the locking rod to move to cause the locking part to unlock the first sub-locking unit. The locking part may lock the first sub-locking unit when the elastic part drives the locking part to be reset.

In some embodiments, the locking part may include a first plug plate that is configured to rotate around a fixed hinge point. A connection point of the locking rod and the first plug plate do not overlap with the fixed hinge point. The locking rod may drive the first plug plate to lock or unlock the first sub-locking unit when the locking rod moves.

In some embodiments, the first sub-locking unit may include a first plug slot, and the first plug plate may be engaged with the first plug slot to lock or disengaged from the first plug slot to unlock the first sub-locking unit.

In some embodiments, the locking part may include a plug socket. The plug socket may be connected to the loading unit. The first plug plate may be rotatably connected to the plug socket. The fixed hinge point may be formed at a rotation connection point of the first plug plate and the plug socket. The elastic part may be disposed between the first plug plate and the plug socket.

In some embodiments, the locking part may include a connection plug. The locking rod may be operably connected to the connection plug. The locking rod may drive the connection plug to move to lock or unlock the first sub-locking unit.

In some embodiments, the locking part may include a rotation shaft, a rotation disk, a first pin, and a second pin. The rotation shaft may rotate relative to the loading unit. The rotation disk may be sleeved on the rotation shaft. The first pin may be connected to a first side of the rotation disk. The second pin may be connected to a second side of the rotation disk. An axis of the first pin may be not coincident with an axis of the second pin. The first pin may be connected to the locking rod via a hinge connection mode. The second pin may be connected to the connection plug via a hinge connection mode. The elastic part may include a torsion spring, two ends of the torsion spring being connected to the rotation shaft and the loading unit, respectively.

In some embodiments, the first sub-locking unit includes one or more jacks, and the connection plug may be inserted into the one or more jacks to lock the first sub-locking unit.

In some embodiments, one of the first lock and the second lock may include a second plug plate. The other of the first lock and the second lock may include a second plug slot. The second plug plate may be inserted into the second plug slot. The first sub-locking unit may pass through the second plug slot and the second plug plate to lock the first lock and the second lock. The first lock may include a third plug plate. The second lock may include a fourth plug plate. The first sub-locking unit may pass through the third plug plate and the fourth plug plate to lock the first lock and the second lock.

In some embodiments, the loading unit may include a slot. The external component may be loaded within the slot. The slot may include a position limiting part, and the position limiting part may be configured to lock or unlock the external component.

According to another aspect of the present disclosure, a medical imaging system is provided. The medical imaging system may include the gantry as descried above, and the radiation assembly may be disposed on the swing section of the gantry.

According to another aspect of the present disclosure, a safety protection section is provided. The safety protection section may include a loading unit and a lock assembly. The loading unit may be configured to load an external component. The lock assembly may include a first lock, a second lock, a first sub-locking unit, and a second sub-locking unit. The second lock may be disposed on the loading unit. The first sub-locking unit may be configured to lock the first lock and the second lock. The second sub-locking unit may be configured to lock the first sub-locking unit. The external component may drive the second sub-locking unit to unlock the first sub-locking unit when the external component is loaded on the loading unit.

In some embodiments, the second sub-locking unit may include a locking part, a locking rod, and an elastic part. The locking rod may be connected to the locking part. The elastic part may be configured to drive the locking part to be reset. The external component may drive the locking rod to move to cause the locking part to unlock the first sub-locking unit. The locking part may lock the first sub-locking unit when the elastic part drives the locking part to be reset.

In some embodiments, the locking part may include a first plug plate that is configured to rotates around a fixed hinge point. A connection point of the locking rod and the first plug plate may not overlap with the fixed hinge point. The locking rod may drive the first plug plate to lock or unlock the first sub-locking unit when the locking rod moves.

In some embodiments, the first sub-locking unit may include a first plug slot, and the first plug plate may be engaged with the first plug slot to lock or disengaged with the first plug slot to unlock the first sub-locking unit.

In some embodiments, the locking part may include a plug socket. The plug socket may be connected to the loading unit. The first plug plate may be rotatably connected to the plug socket. The fixed hinge point may be formed at a rotation connection point of the first plug plate and the plug socket. The elastic part may be disposed between the first plug plate and the plug socket.

In some embodiments, the locking part may include a connection plug. The locking rod may be operably connected to the connection plug. The locking rod may drive the connection plug to move to lock or unlock the first sub-locking unit.

In some embodiments, the locking part may include a rotation shaft, a rotation disk, a first pin, and a second pin. The rotation shaft may rotate relative to the loading unit. The rotation disk may be sleeved on the rotation shaft. The first pin may be connected to a first side of the rotation disk. The second pin may be connected to a second side of the rotation disk. An axis of the first pin may be not coincident with an axis of the second pin. The first pin may be connected to the locking rod via a hinge connection mode. The second pin may be connected to the connection plug via a hinge connection mode. The elastic part may include a torsion spring. Two ends of the torsion spring may be connected to the rotation shaft and the loading unit, respectively.

In some embodiments, the first sub-locking unit may include one or more jacks, and the connection plug may be inserted into the one or more jacks to lock the first sub-locking unit.

In some embodiments, one of the first lock and the second lock may include a second plug plate. The other of the first lock and the second lock may include a second plug slot. The second plug plate may be inserted into the second plug slot. The first sub-locking unit may pass through the second plug slot and the second plug plate to lock the first lock and the second lock. The first lock may include a third plug plate. The second lock may include a fourth plug plate. The first sub-locking unit may pass through the third plug plate and the fourth plug plate to lock the first lock and the second lock.

In some embodiments, the loading unit may include a slot. The external component may be loaded within the slot. The slot may include a position limiting part, the position limiting part being configured to lock or unlock the external component.

According to another aspect of the present disclosure, a gantry is provided. The gantry may include a main body and an arm. The gantry may further include the safety protection section as described above. The first lock of the safety protection section may be fixedly connected to the main body of the gantry, and the loading unit of the safety protection section may be fixedly connected to the arm of the gantry.

According to still another aspect of the present disclosure, a digital radiography (DR) device is provided. The DR may include a gantry, an arm, a radiation assembly, and the safety protection section as described above. A first end of the arm may be rotatably connected to the gantry, and a second end of the arm may be connected to the radiation assembly. The radiation assembly may be disposed on the loading unit of the safety protection section. The first lock of the safety protection section may be disposed on the gantry.

In some embodiments, the arm may be connected to a gas spring. A first end of the gas spring may be fixedly connected to the gantry. A second end of the gas spring may be configured to drive the arm to rotate relative to the gantry.

According to still another aspect of the present disclosure, a radiation protection method implemented on a terminal device having at least one processor and at least one storage device is provided. The method may include obtaining a distance between a radiation device and the terminal device. The radiation device may be configured to emit radiation. The method may also include determining whether the distance between the radiation device and the terminal device is less than a distance threshold. The method may also include in response to determining whether the distance between the radiation device and the terminal device is less than the distance threshold, transmitting a notification. The distance threshold may be determined based on a radiation dose of the radiation device.

In some embodiments, in response to determining whether the distance between the radiation device and the terminal device is less than the distance threshold, the transmitting a notification may include in response to determining that the distance between the radiation device and the terminal device is less than the distance threshold, transmitting a first notification.

In some embodiments, in response to determining whether the distance between the radiation device and the terminal device is less than the distance threshold, the transmitting a notification may further include in response to determining that the distance between the radiation device and the terminal device is greater than the distance threshold, transmitting a second notification.

In some embodiments, the method may further include obtaining information associated with a user of the terminal device, and determining the distance threshold based on the radiation dose of the radiation device and the information associated with the user of the terminal device. The information associated with the user of the terminal device may indicate whether the user wears a radiation protection suit.

In some embodiments, the obtaining a distance between the radiation device and the terminal device may include receiving a wireless signal, the wireless signal being transmitted by the radiation device, and determining, based on the wireless signal, the distance between the radiation device and the terminal device.

In some embodiments, the determining the distance between the radiation device and the terminal device based on the wireless signal may include determining the distance between the radiation device and the terminal device based on the wireless signal using a wireless ranging technology, the wireless ranging technology including at least one of a BLUETOOTH ranging technology, a WIFI ranging technology, an infrared ranging technology, an ultrawide band (UWB) ranging technology, and a 433 MHz radio frequency signal ranging technology.

In some embodiments, the notification may include at least one of a voice notification, a text notification, an optical notification, a vibration notification, and an audio notification.

In some embodiments, the radiation device may include a mobile radiation device or a portable radiation device.

According to still another aspect of the present disclosure, a radiation protection system is provided. The radiation protection system may include a first receiving module configured to obtain a distance between a radiation device and a terminal device based on a wireless signal. The radiation device may be configured to emit radiation. A first notification module may be configured to transmit a first notification in response to determining that the distance between the radiation device and the terminal device is less than a distance threshold, and transmit a second notification in response to determining that the distance between radiation device and the terminal device is greater than the distance threshold. The distance threshold may be determined based on a radiation dose of the radiation device.

According to still another aspect of the present disclosure, a non-transitory computer readable medium including executable instructions is provided. When executed by at least one processor, the instructions may direct the at least one processor to perform the radiation protection method as described above.

According to still another aspect of the present disclosure, a radiation protection method implemented on a radiation device having at least one processor and at least one storage device is provided. The method may include receiving a wireless signal, the wireless signal being transmitted by a terminal device and determining a distance between the radiation device and the terminal device based on the wireless signal. The method may also include determining whether the distance between the radiation device and the terminal device is less than a distance threshold, and in response to determining whether the distance between the radiation device and the terminal device is less than the distance threshold, transmitting a notification. The distance threshold may be determined based on a radiation dose of the radiation device.

In some embodiments, in response to determining whether the distance between the radiation device and the terminal device is less than the distance threshold, the transmitting a notification may include in response to determining that the distance between the radiation device and the terminal device is less than the distance threshold, transmitting a first notification.

In some embodiments, in response to determining whether the distance between the radiation device and the terminal device is less than the distance threshold, the transmitting a notification may include in response to determining that the distance between the radiation device and the terminal device is greater than the distance threshold, transmitting a second notification.

In some embodiments, the wireless signal may relate to a second distance between the terminal device and the radiation device, and the second distance may be determined by the terminal device.

In some embodiments, the method may further include determining the distance between the radiation device and the terminal device based on the wireless signal using a wireless ranging technology, the wireless ranging technology including at least one of a BLUETOOTH ranging technology, a WIFI ranging technology, an infrared ranging technology, an ultrawide band (UWB) ranging technology, and a 433 MHz radio frequency signal ranging technology.

According to still another aspect of the present disclosure, a radiation protection system is provided. The radiation protection system may include a receiving module, a determination module, and a notification module. The receiving module may be configured to receive a wireless signal. The wireless signal may be transmitted by a terminal device. The determination module may be configured to determine a distance between a radiation device and the terminal device based on the wireless signal, and determine whether the distance is less than a distance threshold. The notification module may be configured to transmit a first notification in response to determining that the distance between the radiation device and the terminal device is less than a distance threshold, and transmit a second notification in response to determining that the distance between radiation device and the terminal device exceeds the distance threshold. The distance threshold may be determined based on a radiation dose of the radiation device.

According to still another aspect of the present disclosure, a non-transitory computer readable medium is provided. The non-transitory computer readable medium may include executable instructions that, when executed by at least one processor, direct the at least one processor to perform the radiation protection method as described above.

According to still another aspect of the present disclosure, a radiation protection system is provided. The radiation protection system may include a terminal device and a radiation device. One of the terminal device and the radiation device may include a wireless signal transmission device, and the other of the terminal device and the radiation device may include a wireless signal receiving device. The one of the terminal device and the radiation device that includes the wireless signal receiving device may be configured to determine a distance between the terminal device and the radiation device based on a wireless signal transmitted by the wireless signal transmission device, determine whether the distance between the terminal device and the radiation device is less than a distance threshold, and transmit a first notification in response to determining that the distance between the radiation device and the terminal device is less than the distance threshold, and/or transmit a second notification in response to determining that the distance between radiation device and the terminal device is greater than the distance threshold. The distance threshold may be determined based on a radiation dose of the radiation device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

Figure 1:
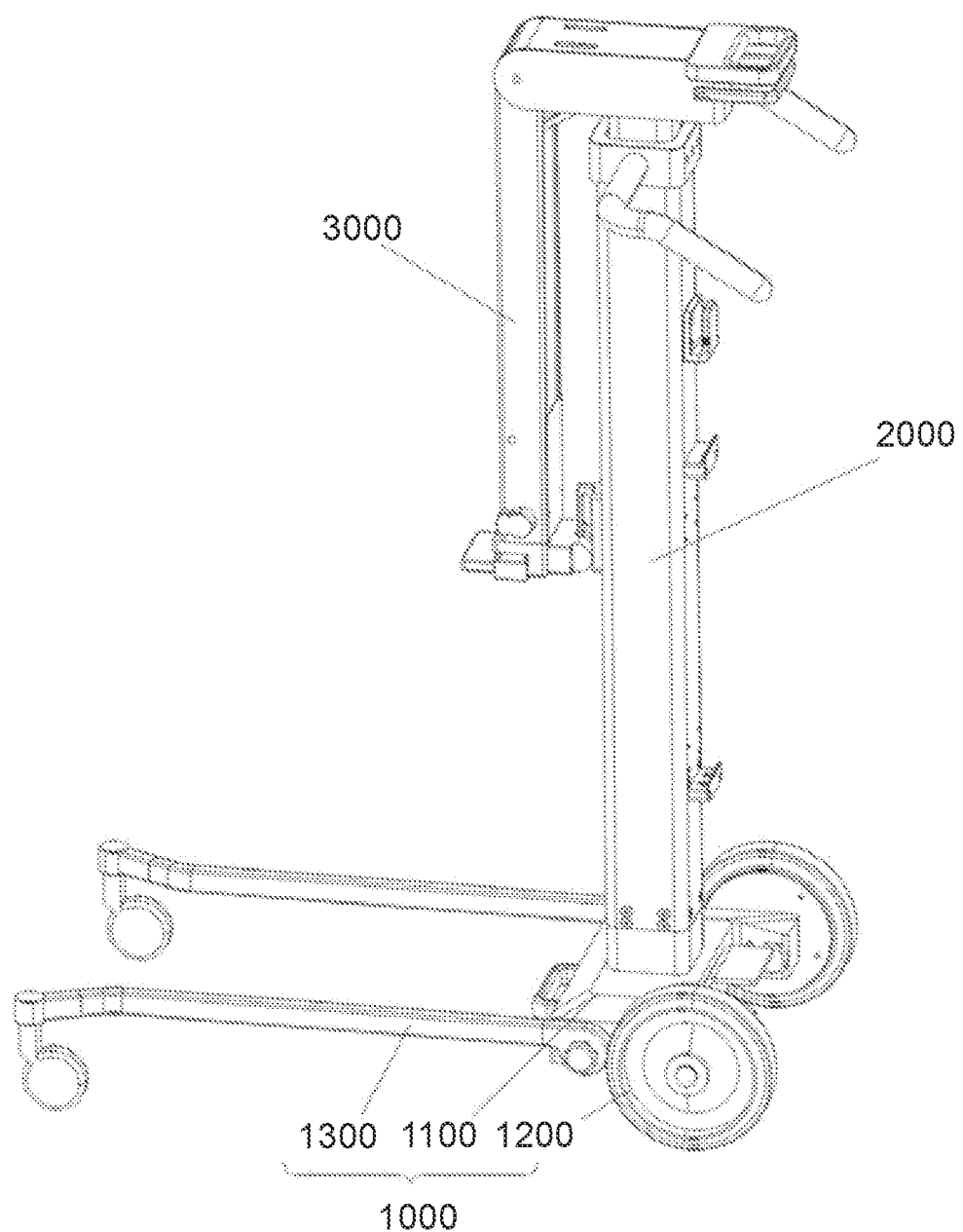
FIG. 1 is a schematic diagram of an exemplary gantry according to some embodiments of the present disclosure.

The reference numerals referred to in the present disclosure include:

- 1000—base section, 1100—base frame, 1200—transfer wheel assembly, 1300—support assembly, 1210—fixing wheel, 1220—movable wheel, 1230—lock assembly, 1231—master rod, 1232—slave rod, 1233—transmission rod, 1234—driving unit, 1310—support rod, 1320—support wheel, 1330—locking unit, 1331—first lock block, 1332—second lock block, 1333—lock nut;
- 2000—lifting section, 2100—fixed sleeve, 2200—support sliding rod, 2300—lifting unit, 2400—first pneumatic support rod;
- 3000—swing section, 3100—swing arm, 3200—support frame, 3300—second pneumatic support rod;
- 4000—safety protection section, 4100—loading unit, 4110—slot, 4120—position limiting part, 4121—position limiting plate, 4122—first spring, 4130—groove, 4140—first part, 4150—second part, 4200—first lock, 4300—first sub-locking unit, 4310—first plug slot, 4320—handle, 4400—second sub-locking unit, 4410—locking part, 4411—first plug plate, 4411-1—plug part, 4412-1—loading plate, 4412-2—pin, 4412-3—opening, 4411'—connection plug, 4412'—rotation shaft, 4413'—rotation disk, 4414'—first pin, 4415'—second pin, 4420—locking rod, 4430—elastic part, 4500—second lock, 4570—second plug slot, 4440—push rod, 4600—second plug plate, 4610—waist-shaped hole;
- 5000—external component, 6000—main body, 7000—arm, 8000—gas spring, 9000—movable base.

Like reference numerals in the present disclosure refer to like structural parts.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules (or units or blocks) may be included in connected logic components, such as gates and flip-flops, and/or can be included in programmable units, such as programmable gate arrays or processors. The modules (or units or blocks) or computing device functionality described herein may be implemented as software modules (or units or blocks), but may be represented in hardware or firmware. In general, the modules (or units or blocks) described herein refer to logical modules (or units or blocks) that may be combined with other modules (or units or blocks) or divided into sub-modules (or sub-units or sub-blocks) despite their physical organization or storage.

It will be understood that when a unit, engine, module, or block is referred to as being "on," "connected to," "coupled to," or "fixed to" another unit, engine, module, or block, it may be directly on, connected, coupled to, or fixed to, or communicate with the other unit, engine, module, or block, or an intervening unit, engine, module, or block may be present, unless the context clearly indicates otherwise. In some embodiments, it may be connected to the other unit, engine, module, or block, through a fixed connection, a detachable connection, a mechanical connection, or an electrical connection. Additionally or alternatively, it may be connected to the other unit, engine, module, or block, via a connection between elements thereof or an interaction therebetween. As used herein, the term "and/or" includes any and all combinations of one or more of the associated listed items.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

In the present disclosure, a first feature being "on" or "under" a second feature may include a direct contact between the first feature and the second feature, or an indirect contact between them, unless expressly stipulated and defined otherwise. Moreover, the first feature being "on," "above," or "on top of" the second feature may include the first feature being directly or obliquely above the second feature, or that the first feature is higher than the second feature. The first feature being "under," "below," or "at the bottom of" the second feature may include the first feature being directly or obliquely below the second feature, or that the first feature is lower than the second feature. Moreover, as used herein, a direction including, e.g., on, above, below, underneath, left, right, etc., indicates the relative positioning of two features when one or more devices on which the two features are supported are positioned as intended for proper operation.

The technical solutions of the present application will be further described below in conjunction with the drawings and embodiments.

A gantry may be used to load and move a radiation assembly. The gantry may use a gas spring as a power source for the movement (e.g., an expansion and rotation) and may have an arm. A gas spring may be connected to the arm to drive the arm to expand or swing. Due to a large elastic force of the gas spring, when the gantry is not provided with the radiation assembly to limit an elastic action of the gas spring, locking the arm using merely a lock catch may be insufficient to counterbalance the elastic force of the gas spring, which may cause the arm to undergo a sudden or unintended movement, e.g., an extension or swing, which in turn may cause an accident such as injuries. When imaging or treating a patient, the radiation assembly may emit radiations that may harm the medical staff. In order to avoid or reduce the radiation exposure, the medical staff may need to stay away from the radiation assembly and control the radiation assembly using a terminal device from distance. However, if the distance exceeds a threshold, a communication between the radiation assembly and the terminal may be affected. Therefore, it is desirable to provide a gantry for loading and supporting a radiation assembly, a safety protection section, and radiation systems, methods, and devices.

FIG. 1 is a schematic diagram of an exemplary gantry for an X-ray system according to some embodiments of the present disclosure. As shown in FIG. 1, the gantry may include a base section 1000, a lifting section 2000, and a swing section 3000. The base section 1000 may be configured to move on a plane. A first end of the lifting section 2000 may be connected to the base section 1000, and a second end of the lifting section 2000 may be disposed opposite to the first end of the lifting section and can be lifted. A first end of the swing section 3000 may be rotatably connected to the second end of the lifting section, and a radiation assembly may be disposed on a second end of the swing section, so that the radiation assembly may swing. In some embodiments, the gantry may be used in an X-ray system. The X-ray system may include a digital radiography (DR) device. In some embodiments, the X-ray system may include a portable digital radiography device.

In the present disclosure, the base section 1000 may meet the requirement of fast movement and fast transition. The lifting section 2000 may adjust a height of the radiation assembly in a large range, so as to adjust a distance between a radiation source and an image receiver or a distance between a focus and the ground. The swing section 3000 may be quickly folded and unfolded. The swing section 3000 may adjust the height of the radiation assembly in a small range. The base section 1000, the lifting section 2000 and the swing section 3000 may cooperate to rapidly position the radiation assembly. The swing section 3000 may be quickly disassembled and assembled with the radiation assembly. In this way, the radiation assembly may be quickly transferred or quickly deployed, and a patient may be quickly imaged or quickly diagnosed, and then the radiation assembly may be quickly transferred to a next patient in a complex environment without sacrificing imaging requirements.

In some embodiments, the base section 1000 may include a base frame 1100, a transfer wheel assembly 1200, and a support assembly 1300. The lifting section 2000 may be connected to the base frame 1100. The transfer wheel assembly 1200 may be disposed on the base frame 1100. The base frame 1100 may be configured to move on the plane via the transfer wheel assembly 1200. The support assembly 1300 may be rotatably connected to the base frame 1100. The support assembly 1300 may be lifted when the gantry is moved. Therefore, when the base frame 1100 is moved to a desired position by the transfer wheel assembly 1200, the support assembly 1300 may be put down to abut the ground and support the base frame 1100, so that the base frame 1100 may support the lifting section 2000, the swing section 3000, and the radiation assembly on the swing section 3000 safely and reliably.

In some embodiments, the base section 1000 may include a base frame 1100 and transfer wheel assembly 1200. An area of the base frame 1100 in a horizontal direction may be set larger. A count of the transfer wheel assembly 1200 may be set to more than three, so as to ensure that the base frame 1100 may safely and reliably support the lifting section 2000, the swing section 3000, and the radiation assembly on the swing section 3000. Preferably, the base frame 1100 may have a rectangular plate structure, the count of transfer wheel assembly 1200 may be four, and the four transfer wheel assemblies 1200 may be disposed on four corners of the base frame 1100.

In some embodiments, the transfer wheel assembly 1200 may include a universal wheel and/or a straight wheel.

Figure 2:
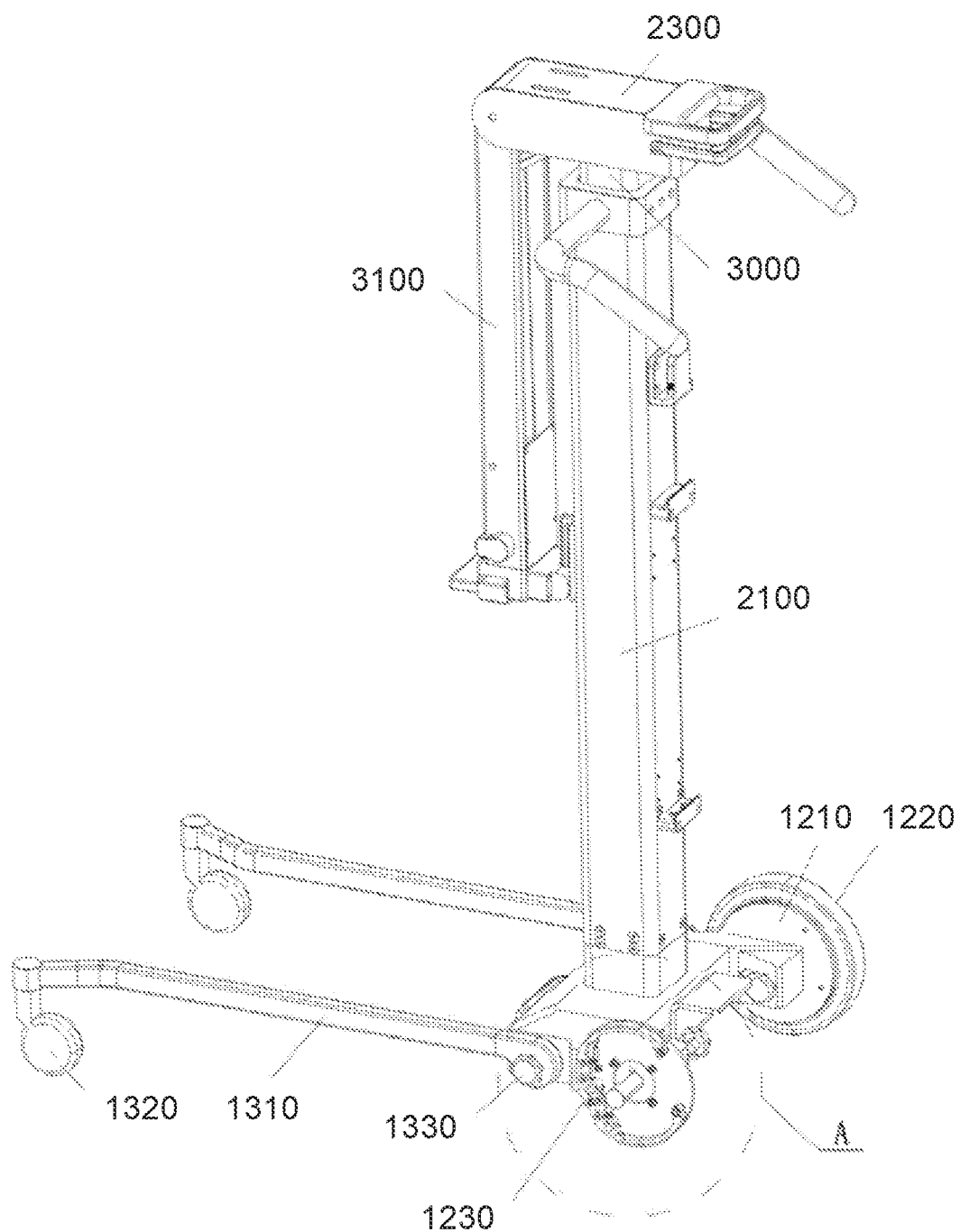
FIG. 2 is a schematic diagram of another exemplary gantry according to some embodiments of the present disclosure.

FIG. 2 is a schematic diagram of another exemplary gantry according to some embodiments of the present disclosure. As shown in FIG. 1-2, in some embodiments, the transfer wheel assembly 1200 may include a fixing wheel 1210, a movable wheel 1220, and a lock assembly 1230. The fixing wheel 1210 may be fixedly connected to the base frame 1100. The movable wheel 1220 may be rotatably connected to the base frame 1100, and may receive the fixing wheel 1210 therein. The lock assembly 1230 may be connected to the fixing wheel 1210 and have a locked configuration and an unlocked configuration. In the locked configuration, the lock assembly 1230 may interfere with the rotation of the movable wheel 1220, and the movable wheel 1220 is stationary relative to the fixing wheel 1210. In the unlocked configuration, the movable wheel 1220 can rotate relative to the fixing wheel 1210. The lock assembly 1230 may be configured to control a movement of the movable wheel 1220 such that the movable wheel 1220 is static relative to the fixing wheel 1210 when the lock assembly 1230 is in a locked configuration. The lock assembly 1230 may be configured to control the movement of the movable wheel 1220 such that the movable wheel 1220 moves relative to the fixing wheel 1210 when the lock assembly 1230 is in an unlocked configuration. In this way, the movable wheel 1220 may be locked by the lock assembly 1230 when the base frame 1100 is moved to a desired position through the movable wheel 1220, so as to avoid the base section 1000 from sliding during a diagnosis process.

Figure 3:
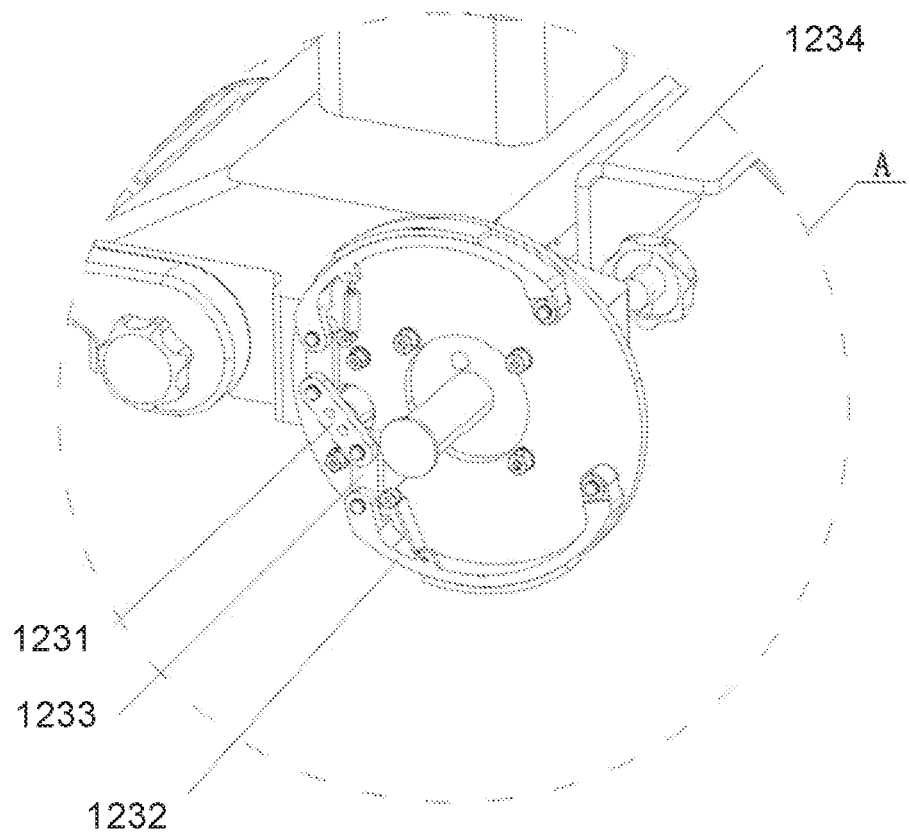
FIG. 3 is an enlarged schematic diagram of a part A shown in FIG. 2 according to some embodiments of the present disclosure.

FIG. 3 is an enlarged schematic diagram of a part A shown in FIG. 2 according to some embodiments of the present disclosure. As shown in FIG. 3, in some embodiments, the lock assembly 1230 may include a master rod 1231, a slave rod 1232, a transmission rod 1233, and a driving unit 1234. The master rod 1231 may be disposed on the fixing wheel 1210 via a rotation shaft. The slave rod 1232 may include a fixing end and a rotation end. The fixing end may be rotatably connected to the fixing wheel 1210. A first end of the transmission rod 1233 may be rotatably connected to the master rod 1231, and a second end of the transmission rod 1233 may be connected to the rotation end of the slave rod 1232. The driving unit 1234 may be connected to the rotating shaft, and may drive a rotation of the master rod 1231. The driving unit 1234 may be configured to cause the slave rod 1232 to press against an inner wall of the movable wheel 1220 via the transmission rod 1233, when the rotation of the master rod 1231 causes the lock assembly 1230 to be in the locked configuration. The driving unit 1234 may also be configured to disengage the slave rod 1232 from the movable wheel 1220 via the transmission rod 1233, when the rotation of the master rod 1231 causes the lock assembly 1230 to be in the unlocked configuration.

Figure 4:
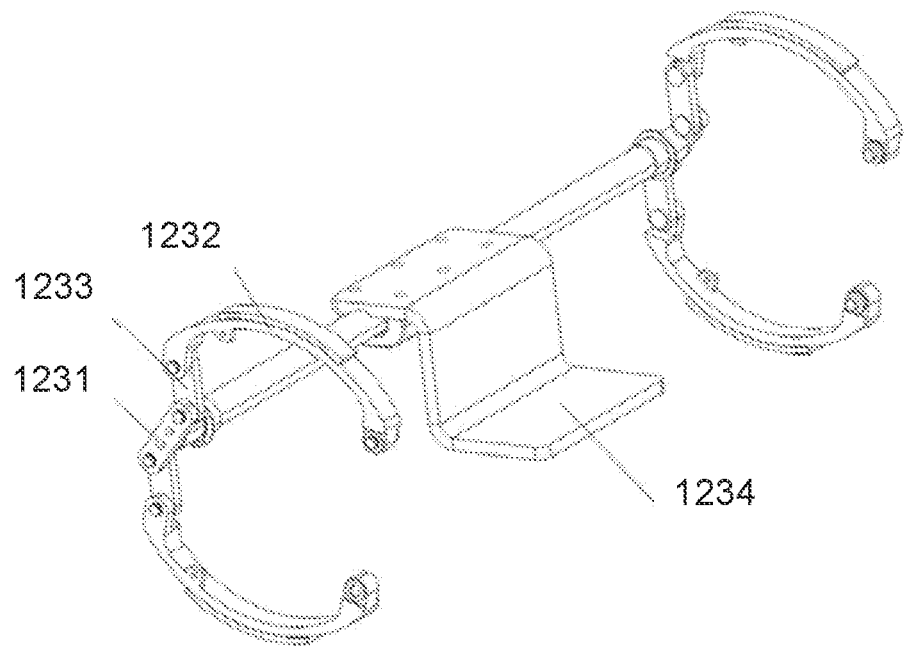
FIG. 4 is a schematic diagram of an exemplary lock assembly according to some embodiments of the present disclosure.

FIG. 4 is a schematic diagram of an exemplary lock assembly according to some embodiments of the present disclosure. As shown in FIGS. 3 and 4, in some embodiments, the master rod 1231 may be rotatably disposed on the base frame 1100 by making the middle part of the master rod 1231 pass through the fixing wheel 1210 via the rotating shaft. Two ends of the master rod 1231 may be connected to the transmission rod 1233. Each transmission rod 1233 may be configured with one slave rod 1232. The outer side of each slave rod 1232 may be provided with a friction pad. The rotation of the master rod 1231 may simultaneously drive two transmission rods 1233 that are connected to the two ends of the master rod 1231, thereby causing two slave rods 1232 that are connected to the two transmission rods 1233 to expand or retract. The friction pads on the two slave rods 1232 may interfere with the movable wheel 1220. In addition, the slave rod 1232 may also be connected to the fixing wheel 1210 through a stop spring, which may stop the slave rod 1232 at a position corresponding to the locked configuration position or the unlocked configuration.

As shown in FIG. 4, in some embodiment, the transfer wheel assembly 1200 may include a first transfer wheel and a second transfer wheel. The first transfer wheel may be disposed on a first side of the base frame 1100, and the second transfer wheel may be disposed on a second side of the base frame 1100. The first side of the base frame 1100 may be opposite to the second side of the base frame 1100. A first lock assembly disposed on the first transfer wheel and a second lock assembly disposed on the second transfer wheel may share one driving unit 1234. The driving unit 1234 may be a pedal. When the pedal is stepped down, the lock assembly 1230 may be in the locked configuration, and when the pedal is lifted, the lock assembly 1230 may be in the unlocked configuration.

As shown in FIG. 2, in some embodiments, the support assembly 1300 may include a support rod 1310, a support wheel 1320 and a locking unit 1330. An end of the support rod 1310 may be rotatably connected to the base frame 1100. The support wheel 1320 may be disposed on the other end of the support rod 1310 and configured to support the support rod 1310. The locking unit 1330 may be disposed between the support rod 1310 and the base frame 1100 and configured to lock the support rod 1310 on the base frame 1100 to avoid loosening.

Figure 5:
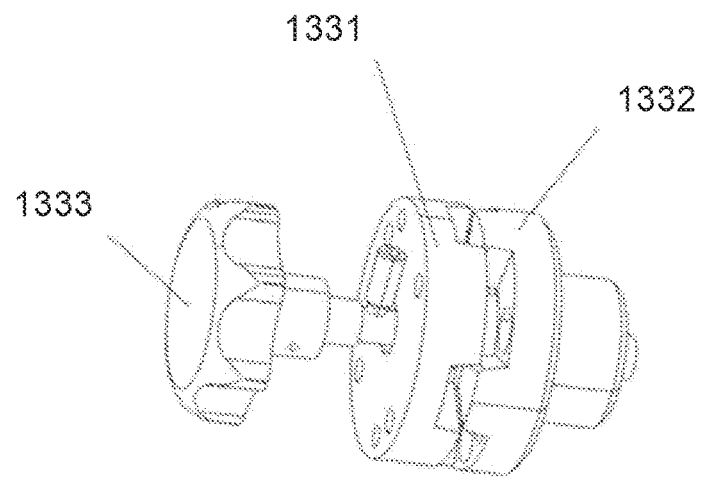
FIG. 5 is a schematic diagram of an exemplary lock unit according to some embodiments of the present disclosure.

FIG. 5 is a schematic diagram of an exemplary lock unit according to some embodiments of the present disclosure.

As shown in FIG. 5, in some embodiments, the locking unit 1330 may include a first lock block 1331, a second lock block 1332 and a lock nut 1333. The first lock block 1331 may be fixedly connected to the support rod 1310. The first lock block 1331 may include a first protrusion or a first groove. The second lock block 1332 may be fixedly connected to the base frame 1100. The second lock block 1332 may include a second protrusion or a second groove. The lock nut 1333 may be threadedly connected to the base frame 1100. The lock nut 1333 may include a threaded connection that is configured to connect the first lock block 1331 and the second lock block 1332. A rotation of the lock nut 1333 may press the support rod 1310 and the first lock block 1331 to be close to the second lock block 1332, so that the first protrusion engages in the second groove, or the second protrusion engages in the first groove.

In some embodiments, there may be two locking units 1330, which are disposed on opposite sides of the base frame 1100, respectively.

Figure 6:
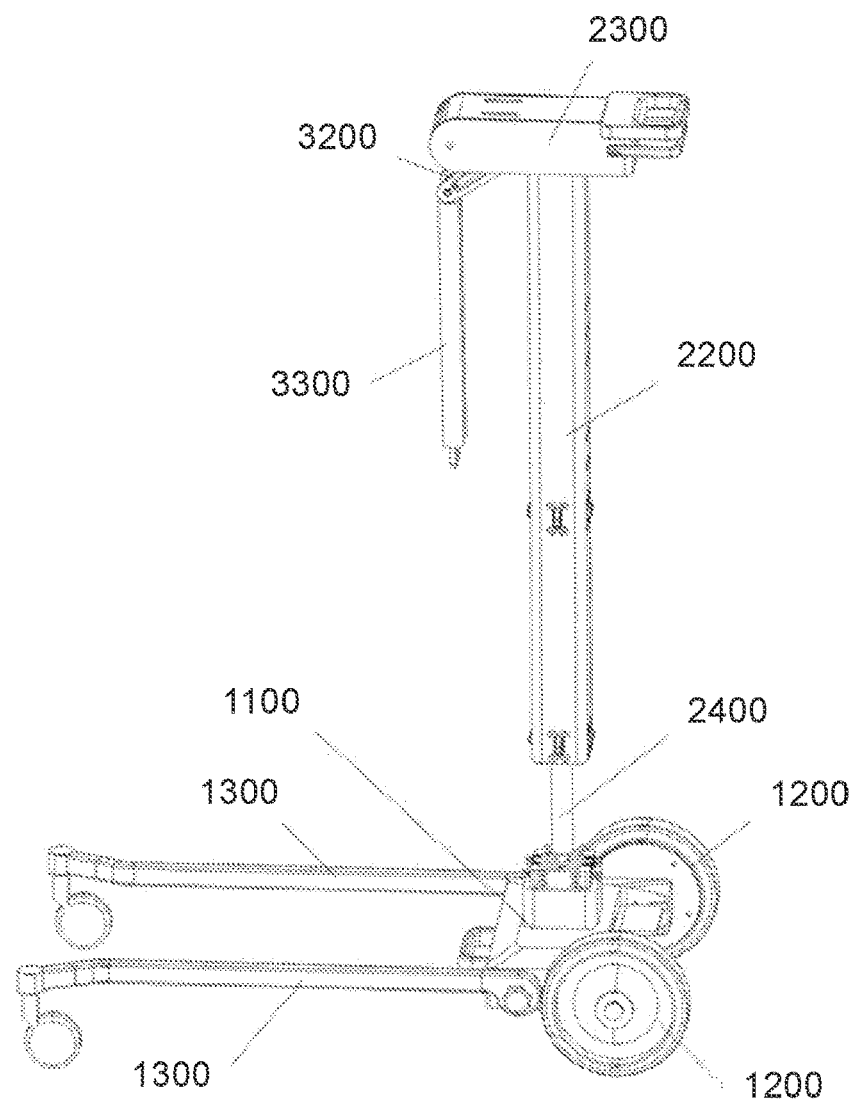
FIGS. 6 and 7 are schematic diagrams of an exemplary gantry according to some embodiments of the present disclosure.
Figure 7:
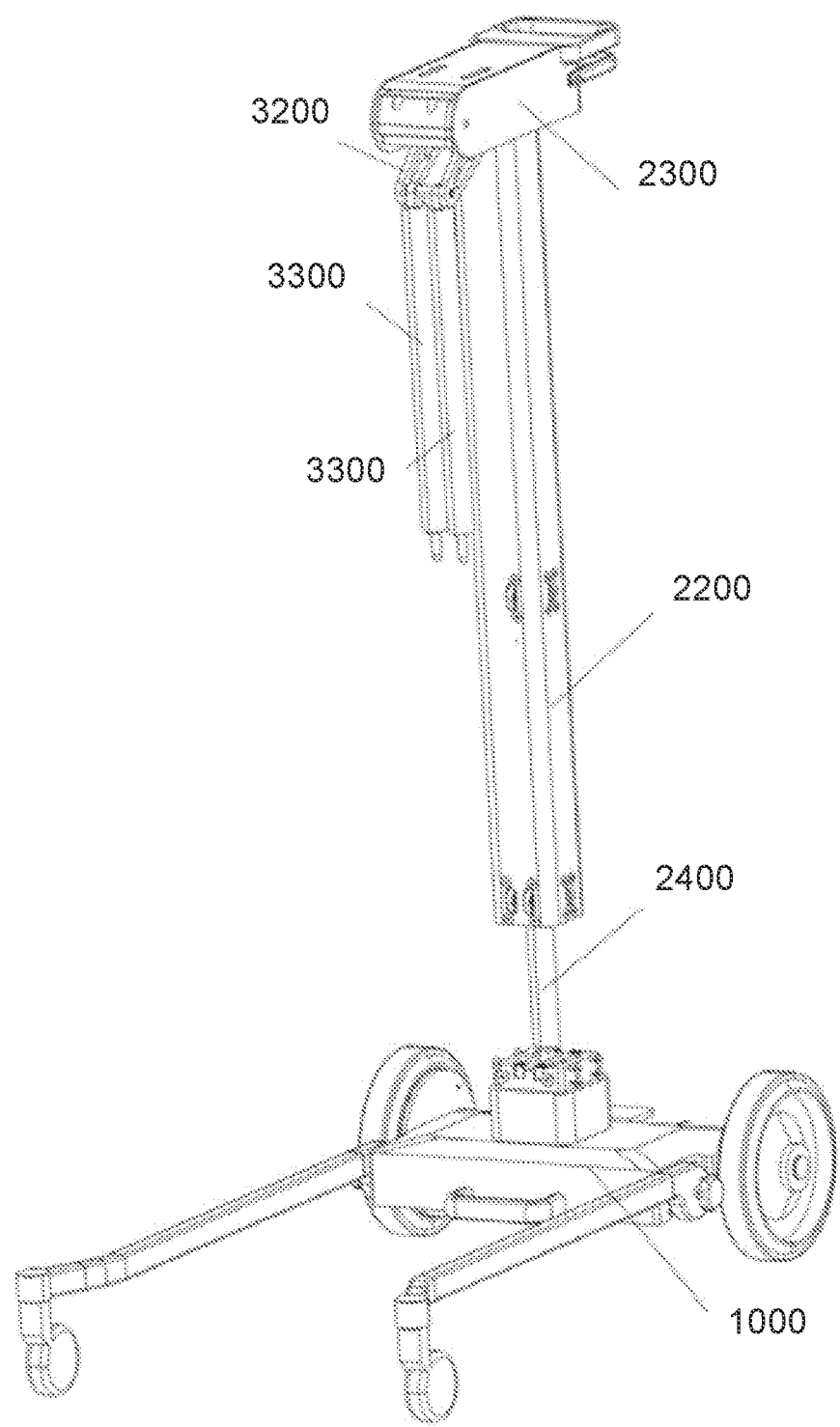

FIGS. 6 and 7 are schematic diagrams of an exemplary gantry according to some embodiments of the present disclosure. As shown in FIGS. 2, 6, and 7, in some embodiments, the lifting section 2000 may include a fixed sleeve 2100, a support sliding rod 2200, a lifting unit 2300 and a first pneumatic support rod 2400. A first end of the fixed sleeve 2100 may be fixedly connected to the base section 1000, and a second end of the fixed sleeve is open. The support sliding rod 2200 may be disposed within a chamber of the fixed sleeve 2100. The lifting unit 2300 may be fixedly connected to an end of the support sliding rod 2200. The end of the support sliding rod 2200 may extend beyond the fixed sleeve. The lifting unit 2300 may be connected to the swing section 3000. The first pneumatic support rod 2400 may be disposed within the chamber of the fixed sleeve 2100. A first end of the first pneumatic support rod 2400 may be fixedly connected to the base section 1000, and a second end of the first pneumatic support rod 2400 may be connected to the support sliding rod 2200, which may support the support sliding rod 2200 at any position.

In some embodiments, the lifting section 2000 may include a column and a lifting drive device. The lifting unit 2300 connected to the swing section 3000 may be directly or indirectly connected to the lifting drive device, and the lifting unit 2300 may be slidably connected to the column.

In some embodiments, the lifting drive device may include a driving source and a transmission assembly. The driving source may include a hydraulic cylinder, a pneumatic cylinder, an engine, an electric motor, etc. The transmission assembly may include a worm and rack mechanism, a rack and pinion mechanism, a screw nut, a belt, a chain, a rope, a pulley, or the like, or any combination thereof. In some embodiments, the lifting drive device may include a motor, a sheave, and a rope. A rotating shaft of the sheave may be fixed on the column. The motor may drive the sheave to rotate around its rotating shaft. A first end of the rope may be wound on the sheave, and a second end of the rope may be fixedly connected to the swing section 3000. The rope may pull the swing section 3000 up and down relative to the column, when the motor drives the sheave to rotate. For example, the sheave may be set at the top of the column. When the sheave rotates to wind up the rope, the rope may pull the swing section 3000 up. When the sheave rotates to relax the wound rope, the swing section 3000 may descend due to its gravity.

In some embodiments, the lifting drive device may also include a manual driving device. For example, the lifting drive device may only include a sheave and a rope, and the sheave may be driven to rotate by a hand crank.

As shown in FIGS. 2, 6, and 7, in some embodiments, the swing section 3000 includes a swing arm 3100 and a second pneumatic support rod 3300. A first end of the swing arm 3100 may be rotatably connected to the second end of the lifting section 2000, and the radiation assembly may be disposed on a second end of the swing arm 3100. The second pneumatic support rod 3300 may be disposed between the swing arm 3100 and the lifting section 2000. When the swing arm 3100 swings upward, a pulling force may be exerted on the second pneumatic support rod 3300.

In some embodiments, the swing section 3000 may further include a support frame 3200. The support frame 3200 may be fixedly connected to the second end of the lifting section 2000, and the second pneumatic support rod 3300 may be connected to the second end of the lifting section 2000 through the support frame 3200. The support frame 3200 may enable the second pneumatic support rod 3300 to have a greater telescoping amount when the swing arm 3100 is swinging, thereby supporting the swing arm 3100 more reliably.

The first pneumatic support rod 2400 and the second pneumatic support rod 3300 may be conventional pneumatic support rods, which are powered by high-pressure inert gas, have a constant supporting force during the entire working stroke, and have a buffering effect. The specific structure and working principle will not be repeated here. Two second pneumatic support rods 3300 may be provided herein, so as to support the radiation assembly safer and more reliably.

In some embodiments, the first pneumatic support rod 2400 and the second pneumatic support 3300 may also be replaced by hydraulic devices for support.

In some embodiments, the gantry may also include a swing drive device. The swing drive device may push or pull the swing arm 3100 to rotate around a pivotal connection point between the swing arm and the second end of the lifting section 2000. The swing driving device may include a hydraulic cylinder, a pneumatic cylinder, an engine, an electric motor, etc.

In some embodiments, the gantry may further include a safety protection section that may lock at least one of the lifting section 2000 and the swing section 3000. More descriptions regarding the safety protection section may be found in FIGS. 8-15.

According to some embodiments of the present disclosure a medical imaging system including the radiation assembly and the gantry is provided. The radiation assembly (or a part thereof) may be detachably assembled on the swing section 3000.

In some embodiments, the radiation assembly may include a part of a medical imaging device, e.g., a part of a digital X-ray or radiography (DR) imaging device, a computer tomography (CT) imaging device or a digital breast tomosynthesis (DBT) imaging device, which is not limited here. In some embodiments, a medical imaging component of the medical imaging device may be disposed on the swing section 3000. Exemplary medical imaging components may include a radiation component or a radiation source (such as a tube) of the DR device.

In some embodiments, the radiation assembly may include an X-ray source. For example, the radiation assembly may include an X-ray tube, a high-voltage generator, and a collimator. The swing section 3000 may be provided with the X-ray source, so that the gantry may be used for imaging or radiotherapy. In some embodiments, a radiotherapy component of a radiotherapy device may be disposed on the swing section 3000. The radiotherapy device may include an X-ray therapy device, a linear accelerator, a beta-ray therapy device, a gamma-ray therapy device, and a proton accelerator, or the like. In some embodiments, other medical, industrial, or transportation devices may also be installed on the swing section 3000, so that the gantry may also be used in corresponding medical, industrial, and transportation scenarios. For example, if the second end of the swing section 3000 is provided with a medical lighting lamp, the gantry may be used for medical lighting. As another example, if the second end of the swing section 3000 is provided with a transportation box, the gantry may be used for a product transportation.

This present disclosure relates to a safety protection section. The safety protection section may be applied to a mobile gantry. The safety protection section may be provided with a loading unit and a lock assembly. When an external component is loaded on the loading unit, the safety protection section may be unlocked, so that an arm of the mobile gantry where the external component is located is unlocked relative to the mobile gantry. The external component may include the radiation assembly. Then, the arm may swing freely to change a position of the external component. When the safety protection section is in the locked configuration, the arm may be prevented from telescoping or swinging relative to the mobile gantry, thereby ensuring the safety of the mobile gantry. The mobile gantry used by the safety protection section may include the gantry shown in FIGS. 1-7, a gantry of the radiotherapy device, or a gantry for medical, industrial, or transportation purposes.

Figure 8:
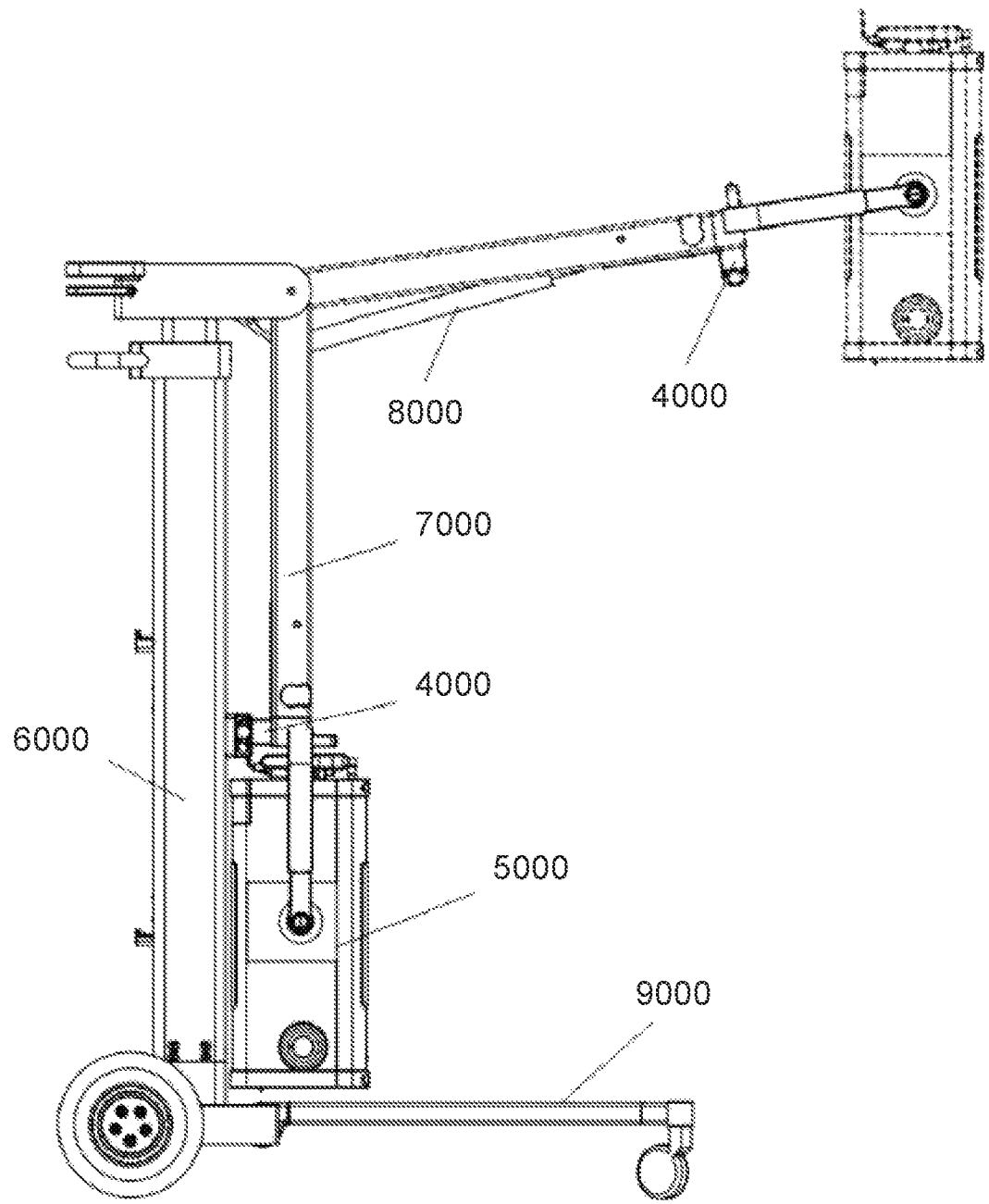
FIG. 8 is a schematic diagram of an exemplary gantry according to some embodiments of the present disclosure.

FIG. 8 is a schematic diagram of an exemplary gantry according to some embodiments of the present disclosure. As shown in FIG. 8, the gantry may be a mobile gantry and include a safety protection section 4000. The safety protection section 4000 is provided between main body 6000 and an arm 7000. The arm 7000 may be connected to a gas spring 8000, and be driven by the gas spring 8000 to telescope or swing. For example, as shown in FIG. 8, the gantry may include a movable base 9000. The main body 6000 may be disposed on the movable base 9000. The arm 7000 may be rotatably connected to the main body 6000. There may be a gas spring 8000 between the arm 7000 and the main body 6000. The gas spring 8000 may drive the arm 7000 to rotate relative to the main body 6000, so that the arm 7000 may move the external component to a certain height for an operator to use. In some embodiments, the gantry may include a medical gantry, and a medical device or a medicine box may be lifted and lowered by the arm 7000 to be used by a medical personnel.

The arm 7000 may be provided with an external component 5000 as required. The safety protection section 4000 may be used to fix the arm 7000 and the external component 5000. In addition, the safety protection section 4000 may also be used to lock the arm 7000, so as to avoid the arm 7000 from telescoping or swinging suddenly, which may cause an accident such as an injury.

In some embodiments, the safety protection section 4000 may be applied to the gantry shown in FIGS. 1-7. The safety protection section 4000 may make the swing section 3000 (or the radiation assembly) of the gantry be locked with the lifting section 2000 of the gantry, thereby effectively preventing the swing section 3000 from accidentally swinging relative to the lifting section 2000.

It should be understood that the safety protection section 4000 in the present disclosure may also be applied to other mechanisms or devices that need to lock a certain component.

Figure 9:
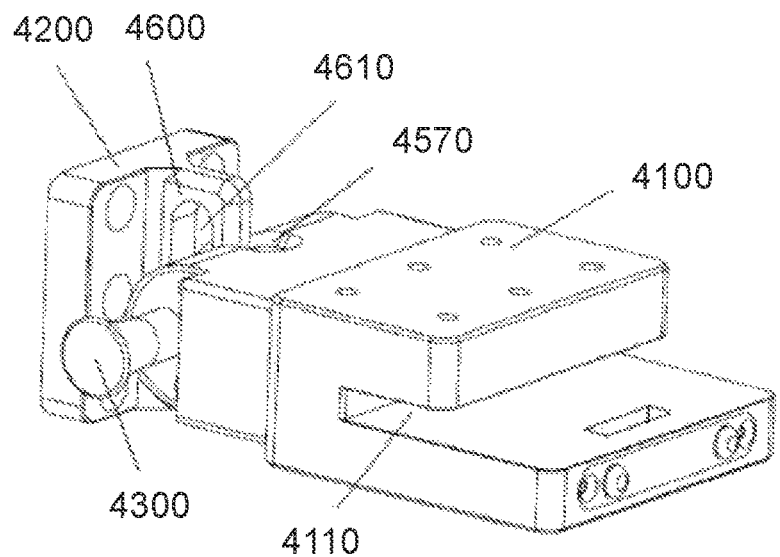
FIG. 9 is a schematic perspective diagram of an exemplary safety protection section according to some embodiments of the present disclosure.

FIG. 9 is a schematic perspective diagram of an exemplary safety protection section according to some embodiments of the present disclosure. As shown in FIG. 9, in some embodiments, the safety protection section 4000 may include a loading unit 4100 and a lock assembly. The loading unit 4100 may be configured to load the external component 5000. The loading unit 4100 may be fixed on the arm 7000 of the gantry. The lock assembly and the loading unit 4100 may lock the arm 7000 of the gantry on the main body 6000 of the gantry.

In some embodiments, the external component 5000 may include an X-ray source assembly. For example, the external component 5000 may include an X-ray tube, a high-voltage generator, and a collimator. The external component 5000 may also include a radiotherapy radiation source assembly, such as an X-ray therapy radiation source assembly, a linear accelerator assembly, a beta-ray therapy radiation source assembly, a gamma-ray therapy radiation source assembly, and a proton accelerator assembly. The external component 5000 may also include other medical, industrial, and transportation devices, so that the safety protection section 4000 may be applied in medical, industrial, or transportation scenarios. In some embodiments, the external component 5000 may be a part of the medical imaging device, the radiotherapy device, or the medical, industrial, and transportation devices.

Figure 10:
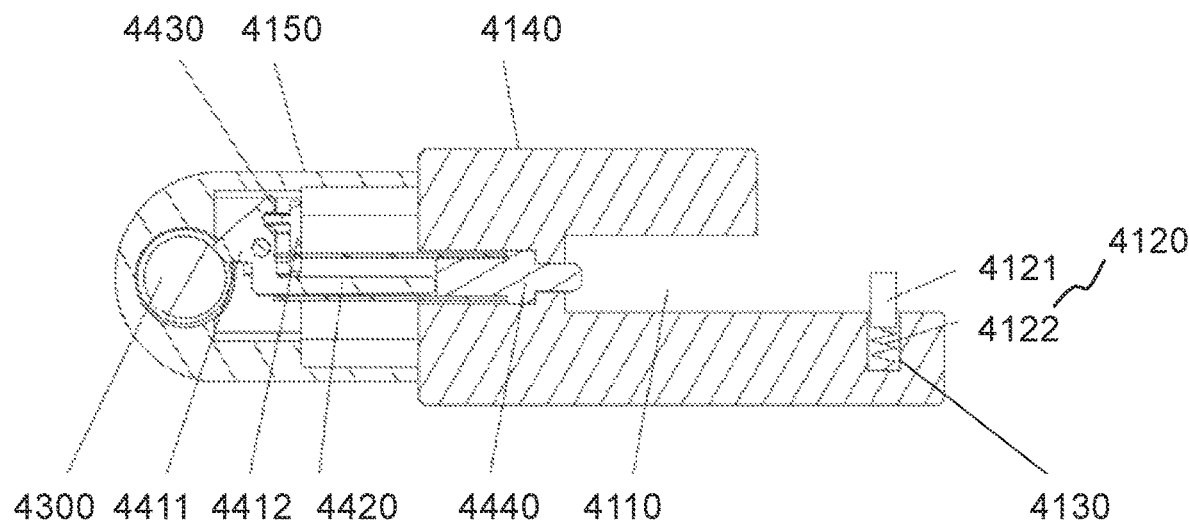
FIG. 10 is a cross-sectional diagram of an exemplary safety protection section according to some embodiments of the present disclosure.
Figure 11:
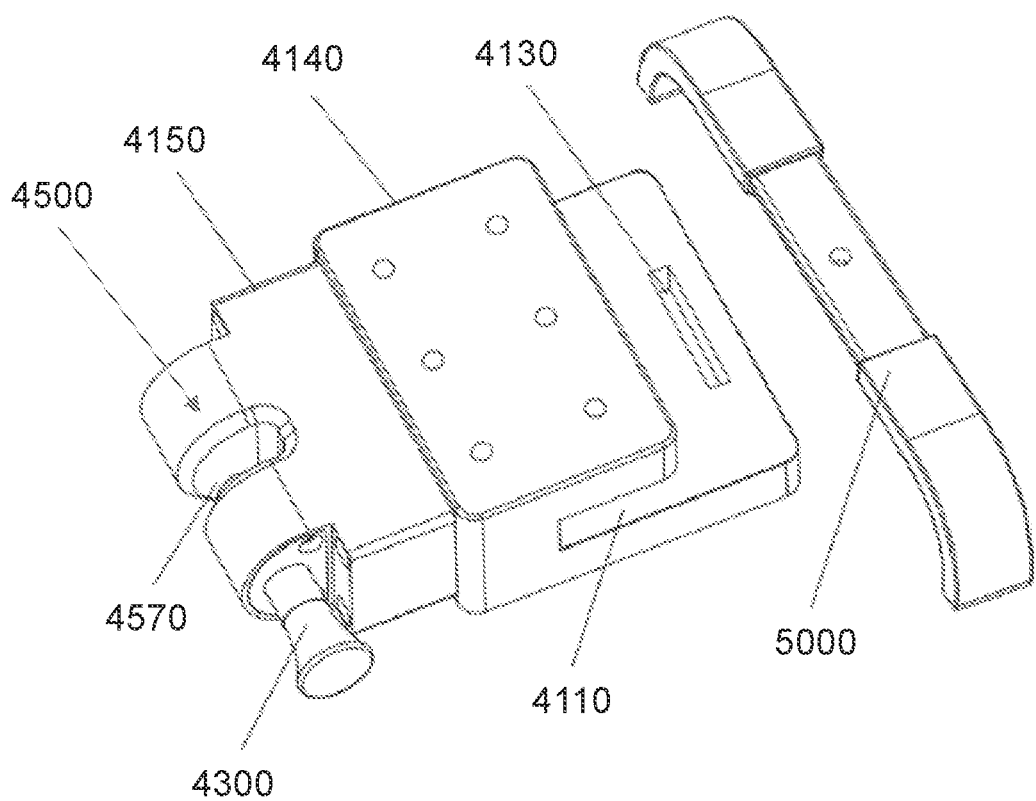
FIG. 11 is a schematic diagram of an exemplary loading unit and an exemplary a first sub-locking unit according to some embodiments of the present disclosure.

FIG. 10 is a cross-sectional diagram of an exemplary safety protection section according to some embodiments of the present disclosure. FIG. 11 is a schematic diagram of an exemplary loading unit and an exemplary a first sub-locking unit according to some embodiments of the present disclosure. As shown in FIGS. 10 and 11, in some embodiments, the loading unit 4100 may be provided with a slot 4110. The slot 4110 may be used to load the external component 5000. That is, the external component 5000 may be loaded within the slot 4110. The slot 4110 may include a position limiting part 4120, and the position limiting part 4120 may be configured to lock the external component 5000 in the slot 4110 after the external component 5000 is loaded within the slot 4110. Optionally, as shown in FIG. 10, the position limiting part 4120 may include a position limiting plate 4121 and a first spring 4122 connected to the position limiting plate 4121. A groove 4130 may be provided on a side wall of the slot 4110. A first end of the first spring 4122 may be fixed to the bottom of the groove 4130, and a second end of the first spring 4122 may be fixed to the bottom of the position limiting plate 4121. The position limiting plate 4121 may be inserted into the groove 4130. When the external component 5000 is loaded within the slot 4110, the position limiting plate 4121 may be pressed down until its upper surface is flush with the side wall of the slot 4110 where the groove 4130 is provided, so that the external component 5000 sweeps through the groove 4130. At this time, the first spring 4122 may be compressed. After the external component 5000 is clamped into the slot 4110, under the drive of the first spring 4122, the position limiting plate 4121 may partially extend out of the groove 4130, and may be attached to the side wall of the external component 5000, thereby fixing the external component 5000 in the slot 4110. When the external component 5000 needs to be taken off, the external component 5000 may be taken out from the slot 4110 by pressing the position limiting plate 4121.

In some embodiments, the position limiting part 4120 may include a limiting groove and a position limiting component that may be inserted into the limiting groove. During a process for loading the external component 5000 into the slot 4110, the position limiting component may be removed from the limiting groove. After the external component 5000 is placed in the slot 4110, the position limiting component may be inserted into the limiting groove, thereby locking the external component 5000 in the slot 4110. It should be understood that the position limiting part 4120 may include other structures capable of locking the external component 5000 in the slot.

In some embodiments, the loading unit 4100 may include two parts. As shown in FIG. 11, the loading unit 4100 may include a first part 4140 and a second part 4150. The first part 4140 may be provided with the slot 4110. The second part 4150 may be hollow inside and may be used to accommodate a part of the lock assembly 1230.

The lock assembly may include a first lock 4200, a second lock 4500, a first sub-locking unit 4300, and a second sub-locking unit 4400.

The first lock 4200 may be fixed to the main body 6000 or other parts of the mobile gantry. The second lock 4500 may be disposed on one side of the second part 4150 of the loading unit 4100. The first lock 4200 and the second lock 4500 may be used in conjunction. The first sub-locking unit 4300 may be configured to lock the first lock 4200 and the second lock 4500, so as to lock the arm 7000 of the mobile gantry with the main body 6000 or other parts of the mobile gantry.

In some embodiments, the safety protection section 4000 may be applied to the gantry shown in FIG. 1. The first lock 4200 may be fixed on the lifting section 2000 of the gantry. The loading unit 4100 may be fixed on the swing section 3000 of the gantry. The second lock 4500 and the first lock 4200 may be provided on the loading unit 4100, and may be used in conjunction. The first sub-locking unit 4300 may lock the first lock 4200 and the second lock 4500, so as to lock the swing section and the lifting section of the gantry.

In this embodiment, as shown in FIG. 9, the first lock 4200 may include a second plug plate 4600. The second plug plate 4600 may be provided with a waist-shaped hole 4610. The second lock 4500 may include a second plug slot 4570. The second plug plate 4600 may be inserted into the second plug slot 4570. The first sub-locking unit 4300 may pass through the second plug slot 4570 and the waist-shaped hole 4610 on the second plug plate 4600, so as to lock the first lock 4200 and the second lock 4500. Additionally or alternatively, the second plug slot 4570 may also be provided on the first lock 4200, and the second plug plate 4600 may be provided on the second lock 4500. Similarly, the first sub-locking unit 4300 may pass through the second plug slot 4570 and the waist-shaped hole 4610 on the second plug plate 4600, so as lock the first lock 4200 and the second lock 4500. In some embodiments, the second plug plate 4600 may be provided with holes in other shapes, such as a circular hole, an oval hole, a rectangular hole, or other irregular holes.

In some embodiments, a through hole may be provided on the second lock 4500. The first sub-locking unit 4300 may pass through the waist-shaped hole 4610 and the through hole, and then be fixed to the second lock 4500. In some embodiments, the through hole may be a threaded hole, and the first sub-locking unit 4300 may be a screw rod. The screw rod may be threadedly connected with the threaded hole after passing through the waist-shaped hole 4610, so that the first lock 4200 and the second lock 4500 are locked. In some embodiments, both the second lock 4500 and the first lock 4200 may include through holes. The first sub-locking unit 4300 may be a padlock. By making the padlock pass through the two through holes and be locked, the first lock 4200 and the second lock 4500 may be locked. When the first lock 4200 and the second lock 4500 need to be unlocked, the padlock may be unlocked and then removed. It should be understood that the first lock 4200 and the second lock 4500 may be locked in other ways.

In some embodiments, the first lock 4200 may include a third plug plate (not shown in the figures), and the second lock 4500 may include a fourth plug plate (not shown in the figures). The third plug plate may be interlaced with the fourth plug plate. The first sub-locking unit 4300 may pass through the third plug plate and the fourth plug plate to lock the first lock 4200 and the second lock 4500.

In some embodiments, the second lock 4500 may be integrally formed with the second part 4150 of the loading unit 4100. In this case, the second plug slot 4570 or the second plug plate 4600 may be directly provided on the second part 4150.

Figure 12:
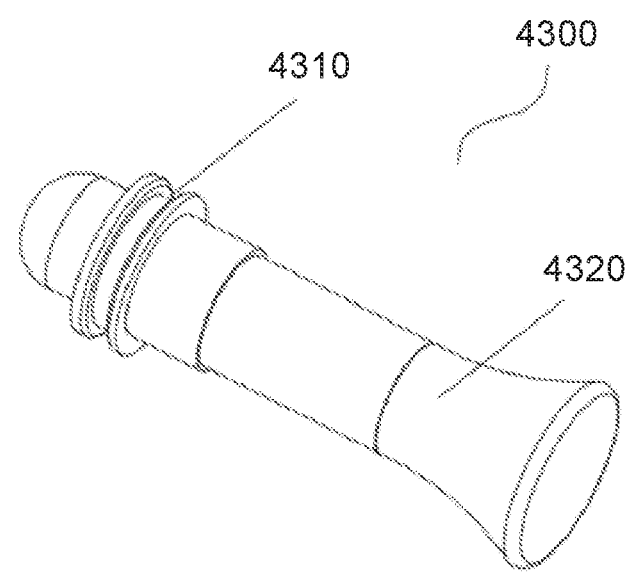
FIG. 12 is a schematic diagram of an exemplary first sub-locking unit according to some embodiments of the present disclosure.

FIG. 12 is a schematic diagram of an exemplary first sub-locking unit according to some embodiments of the present disclosure. As shown in FIG. 12, in some embodiments, the first sub-locking unit 4300 may have a shaft-like structure. A first end of the first sub-locking unit 4300 may pass through the first lock 4200 and the second lock 4500, and a second end of the first sub-locking unit 4300 may be provided with a handle 4320.

Figure 13:
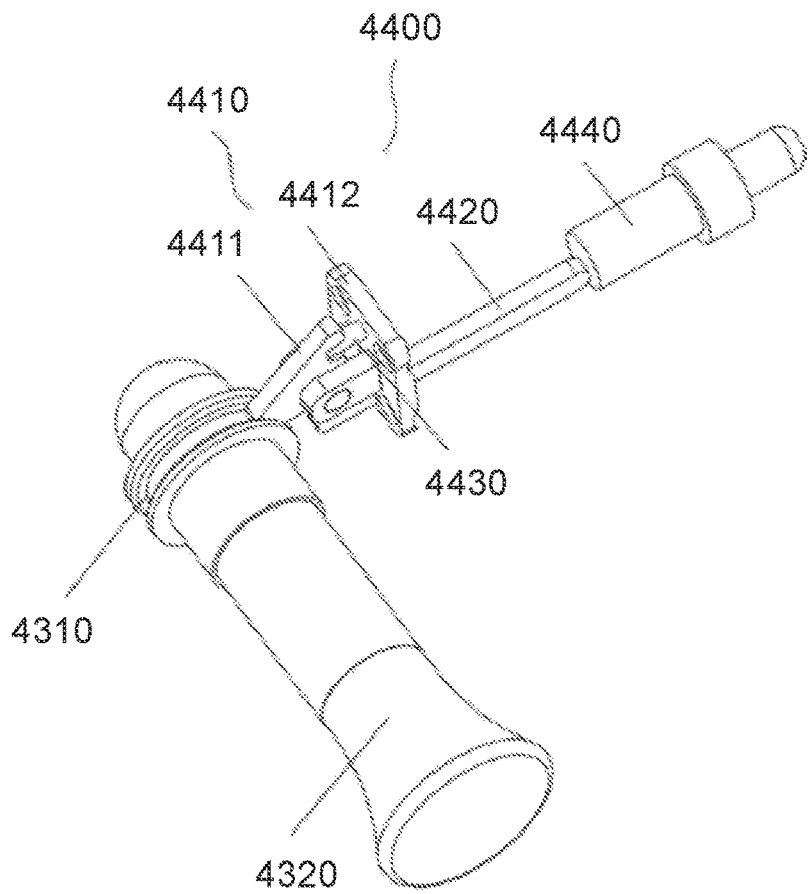
FIG. 13 is a schematic diagram of an exemplary first sub-locking unit and an exemplary second sub-locking unit according to some embodiments of the present disclosure.
Figure 14:
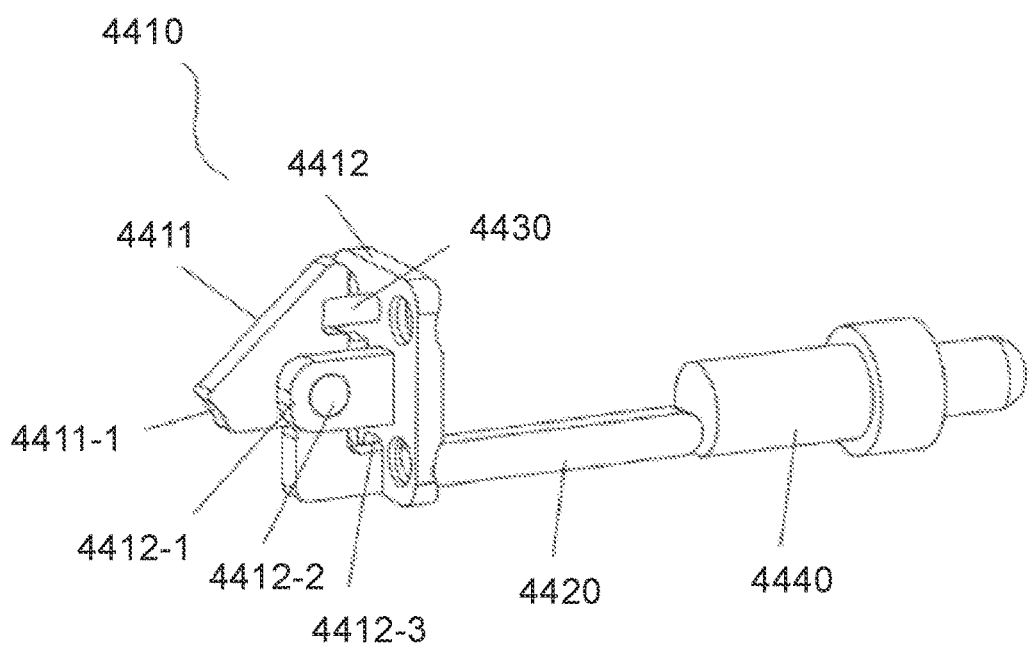
FIG. 14 is a schematic diagram of an exemplary second sub-locking unit according to some embodiments of the present disclosure.

FIG. 13 is a schematic diagram of an exemplary first sub-locking unit and an exemplary second sub-locking unit according to some embodiments of the present disclosure. FIG. 14 is a schematic diagram of an exemplary second sub-locking unit according to some embodiments of the present disclosure. As shown in FIGS. 13 and 14, in some embodiments, the second sub-locking unit 4400 may be configured to lock the first sub-locking unit 4300. When the external component 5000 is loaded on the loading unit 4100, the external component 5000 may drive the second sub-locking unit 4400 to unlock the first sub-locking unit 4300, so that the operator may withdraw the first sub-locking unit 4300 to unlock the first lock 4200 and the second lock 4500.

In some embodiments, when the external component 5000 is loaded on the loading unit 4100, the operator may manually unlock the first sub-locking unit 4300. For example, when the first sub-locking unit 4300 is a screw, the operator may rotate the screw to withdraw the first sub-locking unit 4300.

As shown in FIG. 14, the second sub-locking unit 4400 may include a locking part 4410, a locking rod 4420 connected to the locking part 4410, and an elastic part 4430 that drives the locking part 4410 to reset. The locking part 4410 may include a first plug plate 4411 and a plug socket 4412. The plug socket 4412 may be fixedly installed in the cavity of the second part 4150. The first plug plate 4411 and the plug socket 4412 may be rotatably connected. A fixed hinge point may be formed at a rotation connection point of the plug socket 4412 and the first plug plate 4411. In some embodiments, two loading plates 4412-1 may be provided on the plug socket 4412, a pin 4412-2 may be provided between the two loading plates 4412-1. The pin 4412-2 may pass through the loading plate 4412-1, the first plug plate 4411, and the loading plate 4412-1 in sequence, thereby rotatably connecting the first plug plate 4411 to the plug socket 4412.

One part of the first plug plate 4411 may be connected to the locking rod 4420. A connection point between the locking rod 4420 and the first plug plate 4411 may not overlap with the fixed hinge point. The connection point may be located below the fixed hinge point. When the locking rod 4420 moves, the locking rod 4420 may drive the first plug plate 4411 to rotate around the fixed hinge point, so as to lock and unlock the first sub-locking unit 4300.

In order to better realize the rotation of the first plug plate 4411, an opening 4412-3 may be provided under the plug socket 4412. The locking rod 4420 may pass through the opening 4412-3 and may be connected to the locking part 4410. A height of the opening 4412-3 may be greater than a height of the locking rod 4420. When the locking rod 4420 drives the locking part 4410 to rotate, the opening 4412-3 may prevent the locking rod 4420 from interfering with the plug socket 4412 and affecting the rotation of the locking part 4410.

In some embodiments, the connection point between the locking rod 4420 and the first plug plate 4411 may be located above the fixed hinge point, and the opening 4412-3 may be provided below the plug socket 4412.

An elastic part 4430 may be disposed between the first plug plate 4411 and the plug socket 4412. The elastic part 4430 may drive the first plug plate 4411 to rotate in a reverse direction and to be reset. In some embodiments, the elastic part 4430 may be a spring.

In some embodiments, the elastic part 4430 may be a torsion spring, an elastic sheet, a rubber strip, or the like.

In some embodiments, the locking part 4410 may be provided with a plug part 4411-1, and a first plug slot 4310 may be provided at one end of the first sub-locking unit 4300 that passes through the first lock 4200 and the second lock 4500. When the rod 4420 is moved in a direction toward the locking part 4410 under an external force, the locking rod 4420 may drive the locking part 4410 to rotate relative to the fixed hinge point. At this time, the plug part 4411-1 may be out of the first plug slot 4310, the second sub-locking unit 4400 may unlock the first sub-locking unit 4300, the elastic part 4430 may be compressed. When the locking rod 4420 is not subjected to the external force, the elastic part 4430 may drive the locking part 4410 to rotate in a reverse direction, and make the plug part 4411-1 plug into the first plug slot 4310. In this way, the second sub-locking unit 4400 may lock the first sub-locking unit 4300.

In some embodiments, the external force may be brought by the external component 5000. Optionally, an end of the locking rod 4420 that is not connected to the locking part 4410 may penetrate the slot 4110 of the first part 4140. When the external component 5000 is loaded in within in the slot 4110, the external component 5000 may contact the locking rod 4420 and push the locking rod 4420 to move in a direction toward the first plug plate 4411, thereby driving the first plug plate 4411 to rotate and unlock the first sub-locking unit 4300. When the external component 5000 is taken out, the elastic part 4430 may reset the first plug plate 4411. At this time, the locking rod 4420 may move in a direction away from the first plug plate 4411 and pass through the slot 4110.

In some embodiments, the locking part 4410 may include two position limiting plates that are parallel to each other and spaced apart. The two position limiting plates may be rotatably connected to the plug socket 4412. Two elastic parts 4430 may be provided between each of the position limiting plates and the plug socket 4412. A position limiting boss may be provided at one end of the first sub-locking unit 4300 that passes through the first lock 4200 and the second lock 4500, and the position limiting boss may be circumferentially disposed outside the first sub-locking unit 4300. The position limiting boss may be inserted between the two position limiting plates, so as to lock the first sub-locking unit 4300 by the locking part 4410. When the external component 5000 is loaded within the slot 4110, the external component 5000 may contact the locking rod 4420 and push the locking rod 4420 to move in a direction toward the position limiting plates, and then drive the two limit plates to rotate, thereby unlocking the first sub-locking unit 4300. When the external component 5000 is taken out, the elastic part 4430 may reset the two position limiting plates. At this time, the locking rod 4420 may move in a direction away from the position limiting plates and pass through the slot 4110.

In some embodiment, the second sub-locking unit 4400 may further include a push rod 4440. A first end of the push rod 4440 may abut against the locking rod 4420, and a second end may be a spherical surface and pass through the slot 4110. The external component 5000 may contact the spherical surface, and push rod 4440. The push rod 4440 may push the locking rod 4420 to move in the direction toward the first plug plate 4411. Moreover, the spherical surface may avoid damage to the surface of the external component 5000.

In some embodiments, the second end of the push rod 4440 may in other shapes, for example, a planar shape. The second end of the push rod 4440 may be wrapped with a protective material to avoid damage to the surface of the external component 5000. For example, the protective material may include rubber, soft plastic, etc.

In the safety protection section 4000, when the external component 5000 is not loaded, the first sub-locking unit 4300 may pass through the first lock 4200 and the second lock 4500 to lock the arm 7000 of the gantry to the main body 6000. At this time, one end of the push rod 4440 of the second sub-locking unit 4400 may be a spherical surface that passes through the slot 4110, the position limiting plate 4121 of the position limiting part 4120 may partially extend out of the groove 4130, and the first plug plate 4411 may be engaged with (e.g., inserted into) the first plug slot 4310 of the first sub-locking unit 4300.

When loading the external component 5000 into the slot 4110, the position limiting plate 4121 may be pressed down until its upper end surface is flush with the side wall of the slot 4110 that is provided with the groove 4130. When external component 5000 is clamped into the slot 4110, the position limiting plate 4121 may be driven by the first spring 4122 to partially extend out of the groove 4130, and may be attached to the side wall of the external component 5000, which may fix the external component 5000 in the slot 4110.

At the same time, the external component 5000 may contact the spherical surface of the push rod 4440 and push the push rod 4440 to move in the direction toward the first sub-locking unit 4300. The push rod 4440 may drive the lock rod 4420 to move, the lock rod 4420 may drive the first plug plate 4411 to rotate, and the elastic part 4430 (e.g., a spring) may be compressed. At this time, the first plug plate 4411 may be separated from the first plug slot 4310, the first sub-locking unit 4300 may be withdrawn, and the first lock 4200 and the second lock 4500 may be unlocked. The arm 7000 of the gantry may move or swing freely.

After the external component 5000 is removed, the first sub-locking unit 4300 may be inserted through the first lock 4200 and the second lock 4500, and the first plug plate 4411 may be reversely rotated under the action of the spring to be engaged with (e.g., inserted into) the first sub-locking unit 4300. At this time, the first sub-locking unit 4300 may be locked, and the first lock 4200 and the second lock 4500 may not be separated, so that the arm 7000 of the gantry may be locked on the main body 6000 of the gantry. In this way, the arm 7000 may be prevented from suddenly telescoping or swinging to cause injury, and the safety performance of the gantry may be improved.

Figure 15:
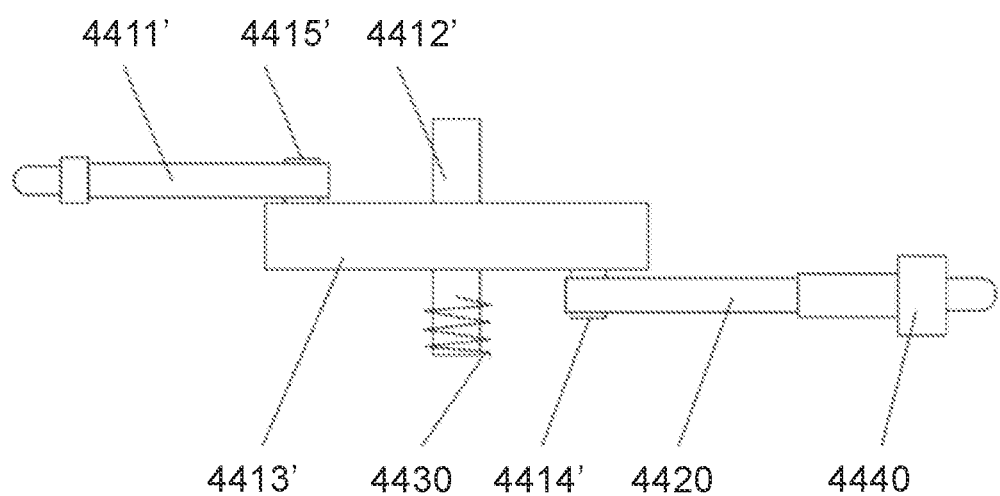
FIG. 15 is a schematic diagram of an exemplary second sub-locking unit according to some embodiments of the present disclosure.

FIG. 15 is a schematic diagram of an exemplary second sub-locking unit according to some embodiments of the present disclosure. In some embodiments, the locking part 4410 of the second sub-locking unit 4400 and the first sub-locking unit 4300 may have structures different from the above-abovementioned embodiment. As shown in FIG. 15, the locking part 4410 may include connection plug 4411', a rotation shaft 4412', a rotation disk 4413', a first pin 4414', and a second pin 4415'.

The rotation shaft 4412' may be rotatably disposed in the loading unit 4100, for example, in the cavity of the second part 4150. An axis of the rotation shaft 4412' may be horizontally arranged. The rotation disk 4413' may be sleeved on the rotation shaft 4412', and an axis of the rotation disk 4413' may be parallel to the axis of the rotation shaft 4412'. The first pin 4414' may be connected to a first side of the rotation disk 4413', and the second pin 4415' may be connected to a second side of the rotation disk 4413'. The axes of the first pin 4414' and the second pin 4415' may be different. The first pin 4414' may be connected to the locking rod 4420 via a hinge connection mode, and the second pin 4415' may be connected to the connection plug 4411' via a hinge connection mode. The elastic part 4430 of the second sub-locking unit 4400 may include a torsion spring. Two ends of the torsion spring may be connected to the rotation shaft 4412' and the loading unit 4100, respectively.

In addition, the first sub-locking unit 4300 may include a jack (not shown in the figure). The connection plug 4411' may be inserted into the jack to lock the first sub-locking unit 4300.

The other components of the embodiment shown in FIG. 15 are the same as the previous embodiments, and will not be repeated.

When the external component 5000 is not provided in the safety protection section 4000, the first sub-locking unit 4300 may pass through the first lock 4200 and the second lock 4500 to lock the arm 7000 of the gantry to the main body 6000. The spherical surface of the push rod 4440 of the second sub-locking unit 4400 may pass through the slot 4110, the position limiting plate 4121 of the position limiting part 4120 may partially extend out of the groove 4130, and the connection plug 4411' may be inserted into the jack of the first sub-locking unit 4300.

During the process for loading the external component 5000 into the slot 4110, the position limiting plate 4121 may be pressed down until its upper surface is flush with the side wall of the slot 4110 that is provided with the groove 4130. The external component 5000 may be clamped into the slot 4110, and the position limiting plate 4121 may be driven by the first spring 4122 to partially extend out of the groove 4130, and may be attached to the side wall of the external component 5000, so as to fix the external component 5000 in the slot 4110.

At the same time, the external component 5000 may contact the spherical surface of the push rod 4440 and push the push rod 4440 to move in the direction toward the first sub-locking unit 4300. The push rod 4440 may drive the locking rod 4420 to move, and the locking rod 4420 may drive the first pin 4414' and the rotation disk 4413' to rotate. When the rotation disk 4413' rotates, the torsion spring may be compressed. At the same time, the rotation disk 4413' may drive the second pin 4415' to rotate, and the second pin 4415' may drive the connection plug 4411' to be separated from the jack. The first sub-locking unit 4300 may be withdrawn, and the first lock 4200 and the second lock 4500 may be unlocked. At this time, the arm 7000 of the gantry may move or swing freely.

After the external component 5000 is removed, the first sub-locking unit 4300 may be inserted through the first lock 4200 and the second lock 4500, and the connection plug 4411' may be reversely rotated under the action of the torsion spring to be inserted into the first sub-locking unit 4300. The first sub-locking unit 4300 may be locked at this time. The first lock 4200 and the second lock 4500 may not be separated, so that the arm 7000 of the gantry may be locked on the main body 6000 of the gantry, which may prevent a sudden or unintended extension or swing of the arm 7000, thereby improving the safety performance of the gantry.

The present disclosure provides a DR device, which is used for X-ray imaging of a patient. The DR device may include the safety protection section 4000, the main body 6000, the arm 7000, the gas spring 8000, and the radiation assembly. A first end of the arm 7000 may be rotatably connected to the main body 6000, and a second end of the arm 7000 may be connected to the radiation assembly. The radiation assembly may emit X-rays and limit the X-rays to a preset area according to a size of a region of the patient for imaging. In some embodiment, the radiation assembly may be the external component 5000.

On the loading unit 4100 of the safety protection section 4000, the first lock 4200 may be fixedly disposed on the main body 6000.

A first end of the gas spring 8000 may be connected to the main body 6000, and a second end of the gas spring 8000 may be connected to the arm 7000. The second end of the gas spring 8000 may drive the arm 7000 to rotate relative to the main body 6000. The arm 7000 may be rotated to be attached to or be parallel to the main body 6000. The arm 7000 may also be rotated to form a certain angle with the main body 6000. The radiation assembly may rotate with the arm 7000 to form two states including a working state and a non-working state.

The gantry may fixedly load and support the radiation assembly. When the radiation assembly is not loaded, the first sub-locking unit 4300 may pass through the first lock 4200 and the second lock 4500 to lock the arm 7000 on the main body 6000. At this time, the gas spring 8000 may be restricted and may not be ejected, which avoids that the arm 7000 is driven by the gas spring 8000 to swing suddenly and cause injuries, thereby improving the safety performance of the gantry.

After being loaded on the gantry, the radiation assembly may drive the second sub-locking unit 4400 to unlock the first sub-locking unit 4300. At this time, the gas spring 8000 may be ejected and drive the arm 7000 to rotate relative to the main body 6000. The arm 7000 may drive the radiation assembly to rotate to a preset position for imaging the patient (a part thereof). The preset position may refer to a position of the radiation assembly where the patient is imaged.

In some embodiments, in order to improve the applicability of the gantry, the main body 6000 may further include a first gantry and a second gantry, wherein the first frame is placed in the second frame. The first gantry may be telescopic relative to the second gantry. The first end of the arm 7000 may be rotatably connected to the second gantry and may move with the second gantry. Through the expansion and contraction of the second gantry relative to the first gantry, a height of the arm 7000 may be adjusted. When patients of different heights or different parts of the patient are imagined, a height of the arm 7000 may be adjusted by adjusting the height of the second gantry, thereby adjusting a height of the radiation assembly. In this way, the radiation assembly may image the patients of different heights or the different parts of the patient. In some embodiments, a roller or a base with the roller may be disposed under the main body 6000, which may make the entire gantry be movable, thereby improving the convenience of the gantry.

The safety protection section 4000 may prevent the arm 7000 from being driven by the gas spring 8000 to suddenly eject, when the radiation assembly is not loaded, thereby ensuring the personal safety of the operator. When needed, by loading the radiation assembly, the safety protection section 4000 may be unlocked, so that the radiation assembly may be driven to the preset position by the arm 7000 to image the patient. Moreover, when the gantry is transported, the radiation assembly may be disassembled. At this time, the arm 7000 may be locked to the main body 6000, which may facilitate the transport of the gantry and avoid damaging the gantry, or a portion thereof.

The present disclosure relates to methods, systems and devices for radiation protection early warning. The methods for radiation protection early warning may be applied to a radiation device (e.g., the X-ray device, the linear accelerator, a C-arm device), and especially may be applied to mobile or portable radiation device. The devices for radiation protection early warning may include a radiation device and a terminal device (e.g., a mobile terminal device). By obtaining a distance between the radiation device and the terminal device and determining whether the distance is less than a distance threshold (e.g., a safe distance), the device for radiation protection early warning may provide users with radiation protection early warning information. Therefore, it may be ensured that the operator is operating out of the distance threshold, and it may also avoid that the operator is too far away from the radiation device to avoid radiation, which may cause an unstable communication between the radiation device and the terminal device and affect the user's control of the radiation device.

In some embodiments, the methods, systems, and devices for radiation protection early warning may be applied in the gantry shown in FIGS. 1-7. Since the gantry is mobile, by applying the methods, systems, and devices for radiation protection early warning in the gantry may secure the safety of the devices and the operator's control of the devices.

Figure 16:
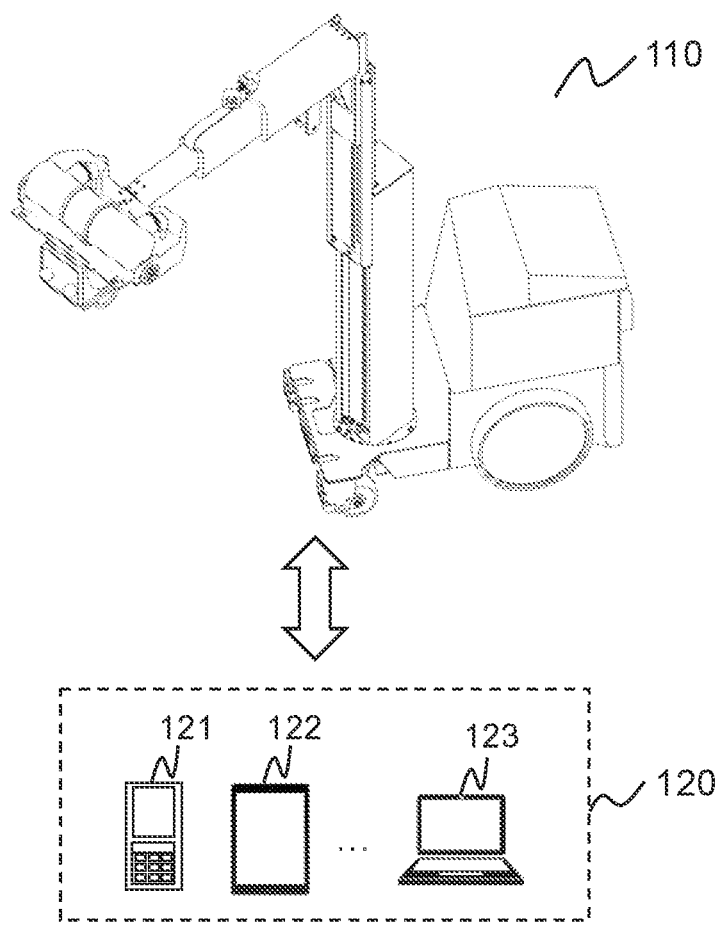
FIG. 16 is a schematic diagram of an exemplary system for radiation protection early warning according to some embodiments of the present disclosure.

FIG. 16 is a schematic diagram of an exemplary system for radiation protection early warning according to some embodiments of the present disclosure. As shown in FIG. 1, the radiation protection system 100 may include a terminal device 120 and a radiation device 110.

The terminal device 120 may be configured to control the radiation device 110 and to display information. In some embodiments, the terminal device 120 may include a handheld terminal 121, a tablet 122, a computer 123, or the like. In some embodiments, the terminal device 120 may include a wireless signal receiving device and/or a wireless signal transmission device. In some embodiments, the wireless signal receiving device and/or the wireless signal transmission device may be built-in or installed on the terminal device 120. For example, the wireless signal receiving device and/or the wireless signal transmission device may be installed (such as clamped) on the terminal device 120 and have a signal connection (e.g., an electrical connection, a wireless connection) with the terminal device 120.

In some embodiments, the terminal device 120 may include a wearable device, a smart mobile device, a virtual reality device, an augmented reality device, or the like, or any combination thereof. In some embodiments, the wearable device may include a smart bracelet, smart glasses, a smart helmet, a smart watch, smart clothes, a smart backpack, or the like, or any combination thereof. In some embodiments, the smart mobile device may include a smart phone, a personal digital assistant (PDA), or the like, or any combination thereof.

Figure 19:
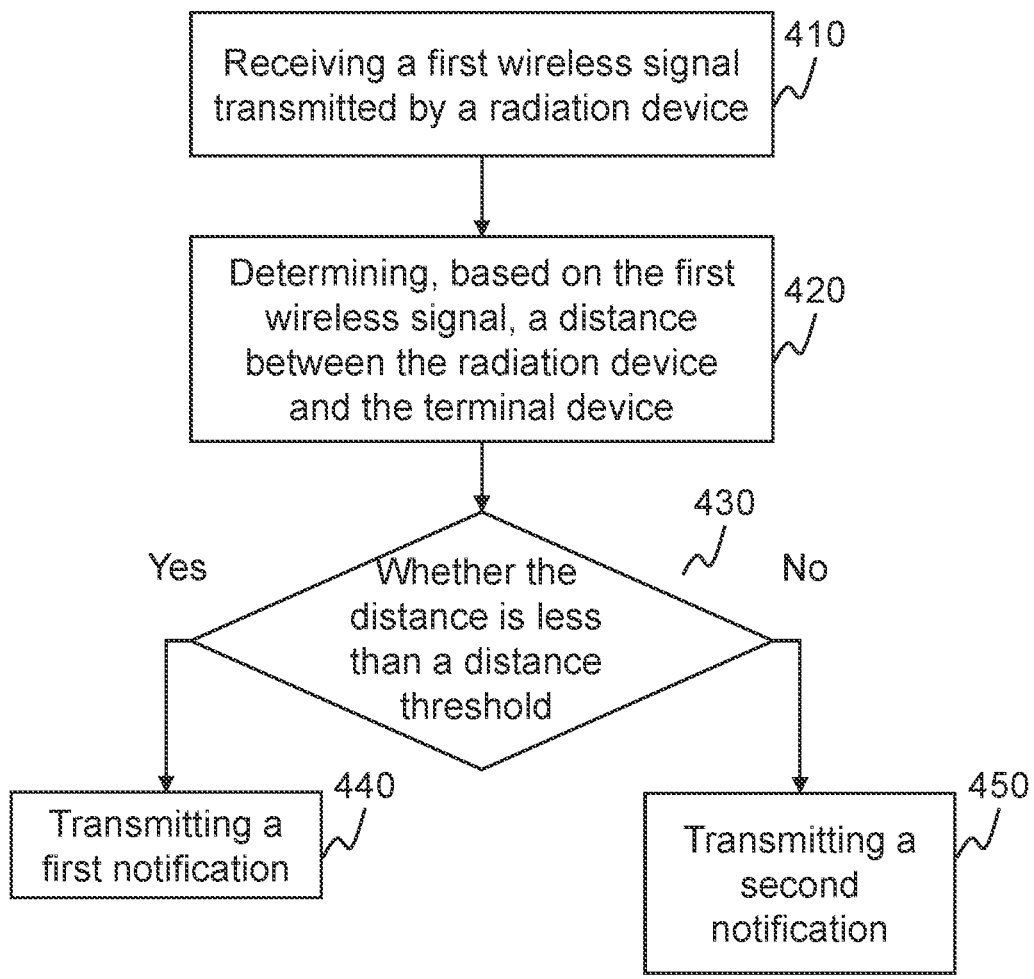
FIG. 19 a flowchart illustrating an exemplary process for radiation protection early warning according to some embodiments of the present disclosure.
Figure 20:
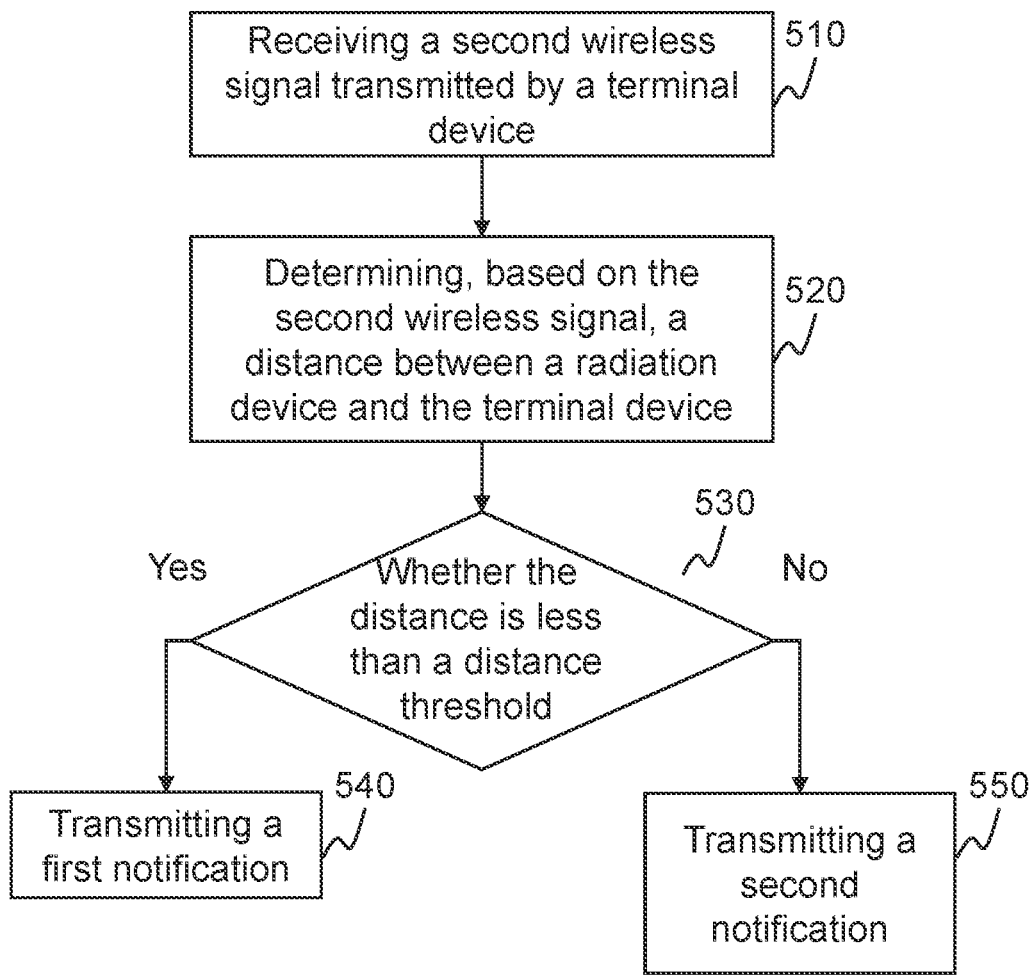
FIG. 20 a flowchart illustrating another exemplary process for radiation protection early warning according to some embodiments of the present disclosure.

In some embodiments, the terminal device 120 may include a processor, and the processor may be used to process information/data relating to the methods for radiation protection early warning described in FIGS. 19 and 20. For example, the processor may be configured to obtain a distance between the radiation device 110 and the terminal device 120. For example, the processor may determine whether the distance is less than a distance threshold. As another example, the processor may control the terminal device 120 to issue an early warning notification and/or a safety notification. In some embodiments, the terminal device 120 may further include a prompt device. The prompt device may include a voice prompt device, a text prompt device, a light prompt device, a vibration prompt device, a video prompt device, or the like, or any combination thereof. For example, the prompt device may include a screen, a speaker, a vibrator, or the like of the terminal device 120. As another example, the prompt device may include a light, a sound, or the like, which have a signal connection with the terminal device 120.

The radiation device 110 may include any device that is able to emit a radiation. For example, the radiation device 110 may include a CT equipment, a positron emission tomography (PET) device, an X-ray device, or the like. In some embodiments, the radiation device 110 may include a mobile radiation device or a portable radiation device. For example, the radiation device 110 may include a mobile X-ray device, a mobile alpha-ray device, a mobile beta-ray device, a mobile gamma-ray device, a mobile proton heavy particle accelerator, or the like. In some embodiments, the radiation device 110 may include a wireless signal transmission device and/or a wireless signal receiving device. In some embodiments, the wireless signal receiving device and/or the wireless signal transmission device may be built or installed on the radiation device 110. For example, the wireless signal receiving device and/or the wireless signal transmission device may be installed (e.g., clamped, fixed) on the radiation device 110, and have a signal connection (such as an electrical connection, a wireless connection, etc.) with the mobile terminal.

In some embodiments, the wireless network between the terminal device 120 and the radiation device 110 may include a wireless local area network (WLAN), a Bluetooth network, an infrared wireless network, a near field communication (NFC) network, or the like, or any combination thereof.

In some embodiments, the radiation device 110 may include a processor. The processor may be configured to process information/data for performing the methods for the radiation protection early warning. For example, the processor may be used to obtain the distance between the radiation device 110 and the terminal device 120. For example, the processor may determine whether the distance is less than the distance threshold. As another example, the processor may control the radiation device 110 to issue an early warning notification and/or a safety notification. In some embodiments, the radiation device 110 may further include a prompt device. The prompt device may include but is not limited to a voice prompt device, a text prompt device, a light prompt device, a vibration prompt device, and a video prompt device, or the like, or any combination thereof. For example, the notification device may include a speaker built in the radiation device 110 or the like. As another example, the prompt device may include an optical device, a sound device, a screen, or the like, which have a signal connection with the radiation device 110.

In some embodiments, the terminal device 120 and the radiation device 110 may include a memory. The memory may be configured to store computer instructions and information/data for performing the methods for radiation protection warning. For example, the memory may be configured to store relevant computer instructions for the methods for radiation protection early warning.

In some embodiments, the terminal device 120 and/or the radiation device 110 may determine the distance therebetween using a wireless signal transmission device and the wireless signal receiving device installed on the terminal device 120 and/or the radiation device 110. The terminal device 120 and/or the radiation device 110 may further transmit a notification to a user by comparing the distance between the terminal device 120 and the radiation device 110 and the distance threshold.

In some embodiments, the terminal device 120 may be provided with the wireless signal receiving device, and the radiation device 110 may be provided with the wireless signal transmission device. In such case, the terminal device 120 may determine the distance between the terminal device 120 and the terminal device 120 according to the wireless signal sent by the wireless signal transmission device of the radiation device 110. The terminal device 120 may also determine whether the distance is less than the distance threshold. If the distance is less than the distance threshold, the terminal device 120 may transmit a first notification (e.g., an early warning notification) to the user, and/or if the distance is greater than or equal to the distance threshold, the terminal device 120 may transmit a second notification (e.g., a safety notification) to the user. In some embodiments, after the terminal device 120 determines the distance between the terminal device 120 and the radiation device 110, the distance may be sent to the radiation device 110. The radiation device 110 may determine whether the distance is less than the distance threshold, and transmit the first and/or second notifications. In some embodiments, the terminal device 120 may also transmit a comparison result between the distance and the distance threshold to the radiation device 110, and the radiation device 110 may transmit the first notification or the second notification.

In some embodiments, the radiation device 110 may be provided with a wireless signal receiving device, and the terminal device 120 may be provided with a wireless signal transmission device. In such case, the radiation device 110 may determine the distance between the radiation device 110 and the terminal device 120 according to the wireless signal transmitted by the wireless signal transmission device of the terminal device 120. The terminal device 120 may also determine whether the distance is less than the distance threshold. If the distance is less than the distance threshold, the radiation device 110 may transmit the first notification, and/or if the distance is greater than or equal to the distance threshold, the terminal device may transmit the second notification. In some embodiments, after the radiation device 110 determines the distance between the terminal device 120 and the radiation device 110, the distance may be sent to the terminal device 120. The terminal device 120 may determine whether the distance is less than the distance threshold, and transmit the first notification and/or the second notification. In some embodiments, the radiation device 110 may also transmit a comparison result between the distance and the distance threshold to the terminal device 120, and the terminal device 120 may transmit the first notification or the second notification.

In some embodiments, the radiation device 110 may include the gantry shown in FIGS. 1-7. The terminal device 120 may control the gantry, so as to display state information of the gantry. For example, the terminal device 120 may control the lifting section 2000 of the gantry to control a height of the lifting unit 2300, so as to control a height of swing section 3000 and a height of the radiation assembly on the swing section 3000. The terminal device 120 may obtain and display the height of the lifting unit 2300. As another example, the terminal device 120 may control the swing drive device of the gantry to control a swing angle of the swing arm 3100, so as to control a height and a horizontal position of the radiation assembly on the swing section 3000. As another example, the terminal device 120 may further obtain and display the swing angle of the swing arm 3100. Optionally, the terminal device 120 may determine the height of the radiation assembly based on the height of the lifting unit 2300 and the swing angle of the swing arm 3100.

In some embodiments, the radiation device 110 may include the safety protection section 4000 shown in FIGS. 9-15. The safety protection section 4000 may be provided with a sensor for sensing whether the safety protection section 4000 is in a locked configuration. The sensor may communicate with the terminal device 120. Merely by way of example, a pressure sensor may be provided on the plug part 4411-1. When the plug part 4411-1 is plugged into the first plug slot 4310, the pressure sensor may determine whether the pressure is greater than a preset threshold, then transmit a signal to the terminal device 120. The terminal device 120 may display that the safety protection section 4000 is in a locked configuration.

Figure 17:
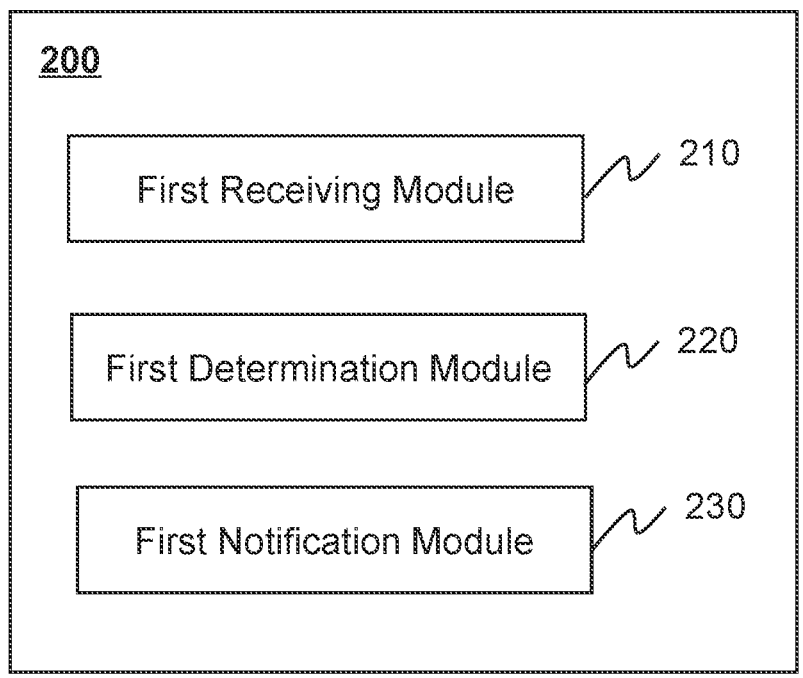
FIG. 17 is a schematic diagram of an exemplary system for radiation protection early warning according to some embodiments of the present disclosure.

FIG. 17 is a schematic diagram of an exemplary system 200 for radiation protection early warning according to some embodiments of the present disclosure. The radiation protection system 200 may be implemented by the terminal device 120 (e.g., the processor thereof). As shown in FIG. 17, the system 200 may include a first receiving module 210, a first determination module 220, and a first notification module 230.

The first receiving module 210 may be configured to receive the first wireless signal sent by the radiation device 110. For example, the first receiving module 210 may control the wireless signal receiving device on the terminal device 120 to receive the first wireless signal.

The first determining module 220 may be configured to determine the distance between the terminal device 120 and the radiation device 110. In some embodiments, the first determining module 220 may determine the distance between the terminal device 120 and the radiation device 110 according to the first wireless signal. For example, the first determining module 220 may use wireless ranging technology to determine the distance between the terminal device 120 and the radiation device 110 according to the first wireless signal.

In some embodiments, the first determination module 220 may determine a first position of terminal device 120 and a second position of the radiation device 110. The first determination module 220 may further determine the distance between the terminal device 120 and the radiation device 110 based on the first and second positions.

The first notification module 230 may be configured to determine whether the distance between the terminal device 120 and the radiation device 110 is less than the distance threshold. If the distance is less than the distance threshold, the first notification may be sent. If the distance is greater than or equal to the distance threshold, the second notification may be sent. For example, the first notification module 230 may control the terminal device 120 (such as the prompt device of the terminal device 120) to send the first and/or second notifications.

Figure 18:
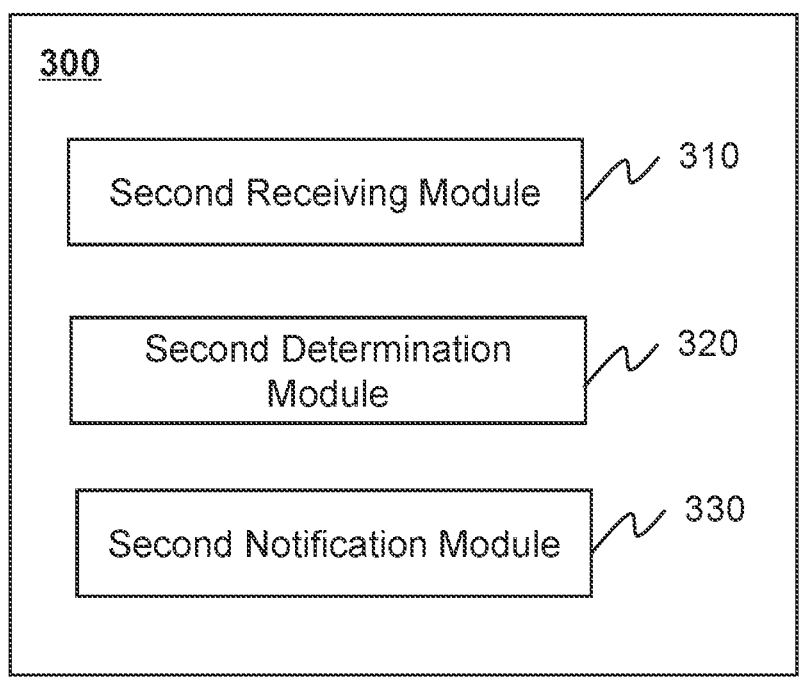
FIG. 18 is a schematic diagram of another exemplary system for radiation protection early warning according to some embodiments of the present disclosure.

FIG. 18 is a schematic diagram of an exemplary system 300 for radiation protection early warning according to some embodiments of the present disclosure. The radiation protection system 300 may be implemented by the radiation device 110 (e.g., the processor thereof). As shown in FIG. 18, the system 300 may include a second receiving module 310, a second determination module 320, and a second notification module 330.

The second receiving module 310 may be configured to receive a second wireless signal sent by the terminal device 120. For example, the second receiving module 310 may control the wireless signal receiving device on the radiation device 110 to receive the second wireless signal.

The second determination module 320 may be configured to determine the distance between the terminal device 120 and the radiation device 110. In some embodiments, the second determination module 320 may determine the distance between the terminal device 120 and the radiation device 110 according to the second wireless signal. For example, the second determining module 320 may use wireless ranging technology to determine the distance between the terminal device 120 and the radiation device 110 according to the second wireless signal.

The second notification module 330 may be configured to determine whether the distance between the terminal device 120 and the radiation device 110 is less than the distance threshold. If the distance is less than the distance threshold, the first notification may be sent. If the distance is greater than or equal to the distance threshold, a second notification may be sent. For example, the second notification module 330 may control the radiation device 110 (such as the prompt device of the radiation device 110) to send the first and/or second notifications.

It should be understood that the systems and modules shown in the FIGS. 17-18 may be implemented in various ways. In some embodiments, the system and the modules may be implemented by hardware, software, or a combination thereof. The hardware part may be realized by dedicated logic. The software part may be stored in a memory and may be executed by an appropriate instruction execution system, such as a microprocessor or dedicated design hardware. Those skilled in the art may understand that the above-mentioned methods and systems may be implemented using computer-executable instructions and/or be included in processor control codes, for example on a carrier medium, such as a disk, CD, or DVD-ROM, a read-only memory (a firmware), a programmable memory, a data carrier (e.g., an optical or electronic signal carrier provides such codes). The system and the modules may not only be implemented by hardware circuits such as a large-scale integrated circuit or a gate array, a semiconductor (e.g., a logic chip, a transistor), a programmable hardware device (e.g., a field programmable gate array, a programmable logic device), etc. It may also be implemented by software that is executed by various types of processors, or may be implemented by a combination of the hardware and software (e.g., firmware).

It should be noted that the above descriptions regarding the systems and the modules are only for description, and do not limit scope of the present disclosure. For persons having ordinary skills in the art, multiple variations and modifications may be made under the teachings of the present disclosure. However, those variations and modifications do not depart from the scope of the present disclosure. For example, the first receiving module 210, the first determination module 220, and the first notification module 230 may be integrated into one module. As another example, the first determination module 220 and the first notification module 230 may be two modules, or one module that may determine the distance between the terminal device 120 and the radiation device 110 and transmit the notification. For example, each module may share the same storage module. As another example, each module may also have its own storage module.

FIG. 19 a flowchart illustrating an exemplary process 400 for radiation protection early warning according to some embodiments of the present disclosure. In some embodiments, the process 400 may be executed by the system 200 applied to the terminal device 120.

In 410, the system 200 (e.g., the first receiving module 210) may receive a first wireless signal transmitted by the radiation device 110.

In some embodiments, the first wireless signal may be transmitted by a wireless signal transmission device on the radiation device 110. The first wireless signal may include a Bluetooth signal, a WIFI signal, an infrared signal, a radio frequency signal, or the like, or any combination thereof. In some embodiments, the radiation device 110 may periodically (for example, every 0.1 seconds) transmit the first wireless signal outwards. In some embodiments, the radiation device 110 may also send the first wireless signal based on a request of the terminal device 120.

In some embodiments, the first receiving module 210 may control the wireless signal receiving device on the terminal device 120 to receive the first wireless signal.

In 420, the system 200 (e.g., the first determination module 220) may determine the distance between the terminal device 120 and the radiation device 110 based on the first wireless signal.

In some embodiments, the first determination module 220 may determine the distance between the radiation device 110 and the terminal device 120 based on the first wireless signal using a wireless ranging technology. In some embodiments, the wireless ranging technology may include a Bluetooth ranging technology, a WIFI ranging technology, an infrared ranging technology, an ultrawide band (UWB) ranging technology, or 433 MHz radio frequency signal ranging technology. In some embodiments, the first determination module 220 may adopt the wireless ranging technology corresponding to the first wireless signal. For example, when the first wireless signal is a Bluetooth signal or a WIFI signal, the first determining module 220 may determine the distance between the radiation device 110 and the terminal device 120 according to a strength of the first wireless signal.

In some embodiments, the first determination module 220 may also determine the distance between the radiation device 110 and the terminal device 120 using other methods. For example, the first determination module 220 may determine the distance between the radiation device 110 and the terminal device 120 using a step sensor on the terminal device 120. The step sensing sensor may be a gyroscope. In some embodiments, the first determination module 220 may determine an account of steps and a step length of a user using the step sensing sensor on the terminal device 120, and thereby determine a distance traveled by the user. Preferably, the first determination module 220 may obtain the account and the step length of steps taken by the user to pick up the terminal device 120 from the radiation device 110 and move away from the radiation device 110, so as to determine the distance between the radiation device 110 and the terminal device 120. As another example, the first determination module 220 may determine the distance between the radiation device 110 and the terminal device 120 using the ultrasonic ranging technology.

In 430, the system 200 (e.g., the first notification module 230) may determine whether the distance is less than the distance threshold.

In some embodiments, the distance threshold may be a safe distance, that is, a distance set to prevent the user from receiving too much radiation. For example, when the distance between the user and the radiation device 110 is greater than the distance threshold, the radiation emitted by the radiation device 110 may not cause harm to the user. In some embodiments, the distance threshold may be determined based on at least a radiation dose or pseudo-radiation dose of the radiation device 110. The radiation dose may refer to an amount of radiation emitted by the radiation device 110 during operation. The pseudo-radiation dose may refer to an amount of radiation that the radiation device 110 is prepared to emit during operation.

In some embodiments, the system 200 may determine the distance threshold based on the radiation dose or pseudo-radiation dose of the radiation device 110 during each operation. In some embodiments, the system 200 may also set the distance threshold to a fixed value. For example, the distance threshold may be a fixed value determined according to an average radiation dose (or a maximum radiation dose) at the radiation device 110. In some embodiments, the distance threshold may be calculated based on the radiation dose or pseudo-radiation dose of the radiation device 110 according to theoretical calculations. In some embodiments, the distance threshold may be obtained based on an actual measurement based on the radiation dose or pseudo-radiation dose of the radiation device 110.

In some embodiments, the system 200 may also obtain information about whether the user that operates the terminal device 120 wears a radiation protection suit. The distance threshold may be determined according to the radiation dose or pseudo-radiation dose of the radiation device 110 and whether the user wears the radiation protection suit. In some embodiments, the terminal device 120 may ask the user whether he/her wears a radiation protection suit (for example, by showing the user questions and options), and the user (for example, a medical staff) may select or input information on the terminal device 120. In some embodiments, if the radiation dose or pseudo-radiation dose on the device side is the same, and the information reflects that the user is not wearing a fire-resistant suit, the distance threshold can be set relatively far. If the information reflects that the user wears the radiation protection suit, the distance threshold may be set relatively close. In some embodiments, the distance threshold may be calculated based on theoretical calculations based on the radiation dose or pseudo-radiation dose of the radiation device 110 and whether the user wears the radiation protection suit. In some embodiments, the distance threshold may be obtained based on actual measurement based on the radiation dose or pseudo-radiation dose of the radiation device 110 and whether the user wears the radiation protection suit.

In some embodiments, if the first notification module 230 determines that the distance between the terminal device 120 and the radiation device 110 is less than the distance threshold, the system 200 may perform operation 440. If the first notification module 230 determines that the distance between the terminal device 120 and the radiation device 110 is greater than or equal to the distance threshold, the system 200 may perform operation 450.

In 440, the system 200 (e.g., the first notification module 230) may transmit the first notification.

In some embodiments, the first notification may include at least one of a voice notification, a text notification, an optical notification, a vibration notification, or an audio notification. For example, the first notification module 230 may control the terminal device 120 (such as the notification device of the terminal device 120) to transmit the voice notification, transmit the text notification on a display screen of the terminal device 120, and simultaneously transmit the vibration notification and the video notification on the terminal device 120.

By transmitting the first notification, the user may be effectively prevented from getting too close to the radiation device 110, thereby effectively ensuring the safety of the user.

In 450, the system 200 (e.g., the first notification module 230) may transmit the second notification.

In some embodiments, the second notification may include at least one of a voice notification, a text notification, an optical notification, a vibration notification, or an audio notification. For example, the first notification module 230 may control the terminal device 120 (such as the notification device of the terminal device 120) to transmit the voice notification, transmit the text notification on a display screen of the terminal device 120, and simultaneously transmit the vibration notification and the video notification on the terminal device 120.

This system 200 may transmit the second notification to the user who has reached the distance threshold to prevent the user from continuing to stay away from the radiation device 110 after reaching the distance threshold. Under the premise of ensuring the safety of the user, the system 200 may also ensure that the terminal device 120 and the radiation device 110 are not so far that the communication therebetween is unstable, thus ensuring a normal operation of the radioactive device (e.g., the radiation device 110).

In some embodiments, the first notification module 230 may control the terminal device 120 to send out the first notification if the distance is less than the distance threshold, or control the terminal device 120 to send out the second notification if the distance is greater than or equal to the distance threshold. In some embodiments, the first notification module 230 may control the terminal device 120 to send out the first notification if the distance is less than the distance threshold, and control the terminal device 120 to send out the second notification if the distance is greater than or equal to the distance threshold. For example, the user holds the terminal device 120 away from the radiation device 110. If the distance is less than the distance threshold (such as 20 m), the first notification module 230 may control the terminal device 120 to send out the first notification. If the distance is greater than or equal to the distance threshold, the first notification module may control the terminal device 120 to send out the second notification. As another example, during the working process of the terminal device 120, the terminal device 120 may move following the user. If the distance changes from greater than the distance threshold to less than the distance threshold, the first notification module 230 may control the terminal device 120 to send out the first notification. If the distance changes from less than the distance threshold to greater than or equal to the distance threshold, the first notification module 230 may control the terminal device 120 to send out the second notification.

FIG. 20 a flowchart illustrating an exemplary process 500 for radiation protection early warning according to some embodiments of the present disclosure. In some embodiments, the process 500 may be executed by the system 300 applied to the radiation device 110.

In 510, the system 300 (e.g., the second receiving module 310) may receive a second wireless signal transmitted by the terminal device 120.

In some embodiments, the second wireless signal may be transmitted by a wireless signal transmission device on the terminal device 120. The second wireless signal may include a Bluetooth signal, a WIFI signal, an infrared signal, a radio frequency signal, or the like, or any combination thereof. In some embodiments, the second receiving module 310 may control the wireless signal receiving device on the radiation device 110 to receive the second wireless signal.

In 520, the system 300 (e.g., the second determination module 320) may determine the distance between the terminal device 120 and the radiation device 110 based on the second wireless signal.

In some embodiments, the second determination module 320 may determine the distance between the radiation device 110 and the terminal device 120 by using the wireless ranging technology based on the second wireless signal. In some embodiments, the second determination module 320 may adopt the wireless ranging technology corresponding to the second wireless signal.

In some embodiments, the second wireless signal may include distance information between the radiation device 110 and the terminal device 120. For example, the terminal device 120 may determine the distance between the radiation device 110 and the terminal device 120 by performing the process 400, and send the distance information to the radiation device 110. In such case, the second determination module 320 may only need to obtain the distance between the radiation device 110 and the terminal device 120 that is included in the second wireless signal.

In 530, the system (e.g., the second notification module 330) may determine whether the distance is less than the distance threshold.

In some embodiments, the distance threshold may be determined based on at least the radiation dose or pseudo-radiation dose of the radiation device 110. In some embodiments, the system 300 may determine the distance threshold based on the radiation dose or pseudo-radiation dose of the radiation device 110 during each operation. In some embodiments, the system 300 may also set the distance threshold to the fixed value. For example, the distance threshold may be the fixed value that is determined according to the average radiation dose (or the maximum radiation dose) at the radiation device 110.

In some embodiments, the system 300 may also obtain information about whether the user that operates the terminal device 120 wears a radiation protection suit. The distance threshold may be determined according to the radiation dose or pseudo-radiation dose at the radiation device 110 and whether the user wears the radiation protection suit.

In some embodiments, if the second notification module 330 determines that the distance between the terminal device 120 and the radiation device 110 is less than the distance threshold, the system 300 may perform operation 540. If the second notification module 330 determines that the distance between the terminal device 120 and the radiation device 110 is greater than or equal to the distance threshold, the system 300 may perform operation 550.

In 540, the system 300 (e.g., the second notification module 330) may transmit the first notification.

In some embodiments, the first notification may include at least one of a voice notification, a text notification, an optical notification, a vibration notification, or an audio notification. For example, the second notification module 330 may control the radiation device 110 (such as the notification device of the radiation device 110) to send out the first notification. By transmitting the first notification, the user may be effectively prevented from getting too close to the radiation device 110, thereby effectively ensuring the safety of the user.

In 550, the system 300 (e.g., the second notification module 330) may transmit the second notification.

In some embodiments, the second notification may include at least one of a voice notification, a text notification, an optical notification, a vibration notification, or an audio notification. For example, the second notification module 330 may control the radiation device 110 (such as the notification device of the radiation device 110) to send out the second notification. This system 300 may transmit the second notification to the user who has reached the distance threshold to prevent the user from continuing to stay away from the radiation device 110 after reaching the distance threshold. Under the premise of ensuring the safety of the user, the system 300 may also ensure that the radiation device 110 and the terminal device 120 are not so far that the communication therebetween is unstable, thus ensuring a normal operation of the radioactive device.

It should be noted that the above description of the processes 400 and 500 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the notification module (such as the first notification module 230 or the second notification module 330) may prompt the user by controlling an external notification device (such as a notification lamp installed in a detection room, a notification speaker, etc.).

The possible beneficial effects of the embodiments of the present disclosure may include but are not limited to: (1) The distance between the terminal device 120 and the radiation device 110 may be accurately determined. (2) The distance threshold may be accurately determined. (3) If the distance between the terminal device 120 and the radiation device 110 is less than the distance threshold, by transmitting the first notification, the user may be effectively prevented from getting too close to the radiation device, thereby effectively ensuring the safety of the user. (4) By transmitting the second notification to the user who has reached the distance threshold, the user may be prevented from continuing to stay away from the radiation device 110 after the distance threshold has been reached. Under the premise of ensuring the safety of the user, the system 300 may also ensure that the radiation device 110 and the terminal device 120 are not so far that the communication therebetween is unstable, thus ensuring a normal operation of the radioactive device. It should be noted that different embodiments may produce different beneficial effects. In different embodiments, the possible beneficial effects may be any one or a combination of the above, or any other beneficial effects that may be obtained.

Having thus described the basic concepts, it may be rather apparent to those skilled in the art after reading this detailed disclosure that the foregoing detailed disclosure is intended to be presented by way of example only and is not limiting.

Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A gantry for an X-ray system, comprising a base section, a lifting section, and a swing section, wherein
   the base section is configured to move, and the base section includes a base frame and a support assembly, wherein
   the support assembly includes a support rod; and
   an end of the support rod is rotatably connected to the base frame;
   a first end of the lifting section is connected to the base section; and
   a first end of the swing section is rotatably connected to a second end of the lifting section, and a radiation assembly is disposed on a second end of the swing section.

2. The gantry of claim 1, wherein
   the base section includes a transfer wheel assembly,
   the lifting section is connected to the base frame, and
   the transfer wheel assembly is connected to the base frame.

3. The gantry of claim 2, wherein
   the transfer wheel assembly includes at least one of a fixing wheel, a movable wheel, or a lock assembly,
   the fixing wheel is fixedly connected to the base frame,
   the movable wheel is rotatably connected to the base frame, and receives the fixing wheel therein, and
   the lock assembly is connected to the fixing wheel and configured to:
   control a movement of the movable wheel such that the movable wheel is static relative to the fixing wheel when the lock assembly is in a locked configuration, and
   control the movement of the movable wheel such that the movable wheel moves relative to the fixing wheel when the lock assembly is in an unlocked configuration.

4. The gantry of claim 3, wherein
   the lock assembly includes at least one of a master rod, a slave rod, a transmission rod, or a driving unit,
   the master rod is disposed on the fixing wheel via a rotation shaft,
   the slave rod includes a fixing end and a rotation end, the fixing end being rotatably connected to the fixing wheel,
   a first end of the transmission rod is rotatably connected to the master rod, and a second end of the transmission rod is connected to the rotation end of the slave rod, and
   the driving unit is connected to the rotation shaft and configured to:
   drive a rotation of the master rod and cause the slave rod to press against the movable wheel when the rotation of the master rod causes the lock assembly to be in the locked configuration, and
   drive the rotation of the master rod and disengage the slave rod from the movable wheel when the rotation of the master rod causes the lock assembly to be in the unlocked configuration.

5. The gantry of claim 3, wherein
the transfer wheel assembly includes a first transfer wheel and a second transfer wheel, the first transfer wheel is disposed on a first side of the base frame, the second transfer wheel is disposed on a second side of the base frame, and the first side of the base frame is opposite to the second side of the base frame, and
a first lock assembly disposed on the first transfer wheel and a second lock assembly disposed on the second transfer wheel share one driving unit.

6. The gantry of claim 2, wherein
the support assembly includes a support wheel and a locking unit,
the support wheel is disposed on the support rod and configured to support the support rod, and
the locking unit is disposed between the support rod and the base frame and configured to lock the support rod on the base frame.

7. The gantry of claim 6, wherein
the locking unit includes a first lock block, a second lock block, and a lock nut,
the first lock block is connected to the support rod and includes a first protrusion or a first groove,
the second lock block is connected to the base frame and includes a second protrusion or a second groove, and
the lock nut includes a threaded connection that is configured to connect the first lock block and the second lock block.

8. The gantry of claim 1, wherein
the lifting section includes a fixed sleeve, a support sliding rod, a lifting unit, and a first pneumatic support rod,
a first end of the fixed sleeve is connected to the base section, and a second end of the fixed sleeve is open,
the support sliding rod is disposed within a chamber of the fixed sleeve,
the lifting unit is connected to an end of the support sliding rod, the end of the support sliding rod extends beyond the fixed sleeve, and the lifting unit is connected to the swing section, and
the first pneumatic support rod is disposed within the chamber of the fixed sleeve, a first end of the first pneumatic support rod is connected to the base section, and a second end of the first pneumatic support rod is connected to the support sliding rod.

9. The gantry of claim 1, wherein
the swing section includes a swing arm and a second pneumatic support rod,
a first end of the swing arm is connected to the second end of the lifting section, and the radiation assembly is disposed on a second end of the swing arm, and
the second pneumatic support rod is disposed between the swing arm and the lifting section, and a pulling force is exerted on the second pneumatic support rod when the swing arm swings upward.

10. The gantry of claim 1, wherein
the gantry further includes a safety protection section, and the safety protection section is configured to lock at least one of the lifting section and the swing section,
the safety protection section includes a loading unit and a lock assembly,
the loading unit is configured to load an external component, the external component including the radiation assembly,
the lock assembly includes a first lock, a second lock, a first sub-locking unit, and a second sub-locking unit,
the second lock is disposed on the loading unit,
the first sub-locking unit is configured to lock the first lock and the second lock,
the second sub-locking unit is configured to lock the first sub-locking unit, and
the external component drives the second sub-locking unit to unlock the first sub-locking unit when the external component is loaded on the loading unit.

11. The gantry of claim 10, wherein
the second sub-locking unit includes a locking part, a locking rod, and an elastic part,
the locking rod is connected to the locking part,
the elastic part is configured to drive the locking part to be reset, and
the external component drives the locking rod to move to cause the locking part to unlock the first sub-locking unit, and
the locking part locks the first sub-locking unit when the elastic part drives the locking part to be reset.

12. The gantry of claim 11, wherein
the locking part includes a first plug plate that is configured to rotate around a fixed hinge point,
a connection point of the locking rod and the first plug plate do not overlap with the fixed hinge point, and
the locking rod drives the first plug plate to lock or unlock the first sub-locking unit when the locking rod moves.

13. The gantry of claim 12, wherein
the first sub-locking unit includes a first plug slot, and
the first plug plate is engaged with the first plug slot to lock or disengaged from the first plug slot to unlock the first sub-locking unit; and
the locking part includes a plug socket, the plug socket being connected to the loading unit,
the first plug plate is rotatably connected to the plug socket,
the fixed hinge point is formed at a rotation connection point of the first plug plate and the plug socket, and
the elastic part is disposed between the first plug plate and the plug socket.

14. The gantry of claim 11, wherein
the locking part includes a connection plug,
the locking rod is operably connected to the connection plug, and
the locking rod drives the connection plug to move to lock or unlock the first sub-locking unit.

15. The gantry of claim 14, wherein
the locking part includes a rotation shaft, a rotation disk, a first pin, and a second pin,
the rotation shaft rotates relative to the loading unit,
the rotation disk is sleeved on the rotation shaft,
the first pin is connected to a first side of the rotation disk,
the second pin is connected to a second side of the rotation disk,
an axis of the first pin is not coincident with an axis of the second pin,
the first pin is connected to the locking rod via a hinge connection mode,
the second pin is connected to the connection plug via a hinge connection mode, and
the elastic part includes a torsion spring, two ends of the torsion spring being connected to the rotation shaft and the loading unit, respectively.

16. The gantry of claim 14, wherein
the first sub-locking unit includes one or more jacks, and
the connection plug is inserted into the one or more jacks to lock the first sub-locking unit.

17. The gantry of claim 10, wherein
one of the first lock and the second lock includes a second plug plate,
the other of the first lock and the second lock includes a second plug slot,
the second plug plate is inserted into the second plug slot, and
the first sub-locking unit passes through the second plug slot and the second plug plate to lock the first lock and the second lock; or
the first lock includes a third plug plate,
the second lock includes a fourth plug plate, and
the first sub-locking unit passes through the third plug plate and the fourth plug plate to lock the first lock and the second lock.

18. The gantry of claim 10, wherein
the loading unit includes a slot,
the external component is loaded within the slot, and
the slot includes a position limiting part, the position limiting part being configured to lock or unlock the external component.

19. The gantry of claim 1, wherein
the base section includes a transfer wheel assembly,
the transfer wheel assembly includes at least one of a fixing wheel, a movable wheel, or a lock assembly,
the lock assembly includes a master rod, two slave rods, and two transmission rods,
the master rod is disposed on the fixing wheel via a rotation shaft,
each of the two slave rods includes a fixing end and a rotation end, the fixing end being rotatably connected to the fixing wheel,
a rotation of the master rod simultaneously drives the two transmission rods that are connected to two ends of the master rod to cause the two slave rods that are connected to the two transmission rods to be expanded or retracted.

20. A medical imaging system, comprising a gantry and a radiation assembly, the gantry including a base section, a lifting section, and a swing section, wherein
the base section is configured to move, and the base section includes a base frame and a support assembly, wherein
the support assembly includes a support rod; and
an end of the support rod is rotatably connected to the base frame;
a first end of the lifting section is connected to the base section;
a first end of the swing section is rotatably connected to a second end of the lifting section; and
the radiation assembly is disposed on a second end of the swing section.

* * * * *